United States Patent
Gebauer et al.

(10) Patent No.: US 10,060,907 B2
(45) Date of Patent: Aug. 28, 2018

(54) REDOXINDICATORS

(71) Applicant: Roche Diagnostics Operations, Inc., Indianapolis, IN (US)

(72) Inventors: Peter Gebauer, Penzberg (DE); Dieter Heindl, Munich (DE); Carina Horn, Biblis (DE); Maksim Fomin, Sindelsdorf (DE)

(73) Assignee: Roche Diagnostic Operations, Inc., Indianapolis, IN (US)

( * ) Notice: Subject to any disclaimer, the term of this patent is extended or adjusted under 35 U.S.C. 154(b) by 0 days.

(21) Appl. No.: 15/438,859

(22) PCT Filed: Aug. 21, 2015

(86) PCT No.: PCT/EP2015/069249
§ 371 (c)(1),
(2) Date: Feb. 22, 2017

(87) PCT Pub. No.: WO2016/026959
PCT Pub. Date: Feb. 25, 2016

(65) Prior Publication Data
US 2017/0191990 A1 Jul. 6, 2017

(30) Foreign Application Priority Data
Aug. 22, 2014 (EP) .................................... 14181964

(51) Int. Cl.
G01N 33/52 (2006.01)
G01N 33/50 (2006.01)
C07D 241/42 (2006.01)
C07D 403/06 (2006.01)

(52) U.S. Cl.
CPC ........... *G01N 33/52* (2013.01); *C07D 241/42* (2013.01); *C07D 403/06* (2013.01); *G01N 33/5005* (2013.01)

(58) Field of Classification Search
CPC .... C07D 241/42; C07D 403/06; G01N 33/52; G01N 33/5005
See application file for complete search history.

(56) References Cited

U.S. PATENT DOCUMENTS

| | | | |
|---|---|---|---|
| 4,919,770 | A | 4/1990 | Preidel et al. |
| 5,108,564 | A | 4/1992 | Szuminsky et al. |
| 5,498,542 | A | 3/1996 | Corey et al. |
| 6,054,039 | A | 4/2000 | Shieh |
| 2005/0023152 | A1 | 2/2005 | Surride et al. |
| 2009/0198117 | A1 | 8/2009 | Cooper et al. |
| 2009/0246808 | A1 | 10/2009 | Wilsey et al. |

FOREIGN PATENT DOCUMENTS

| | | |
|---|---|---|
| EP | 0 821 234 A2 | 1/1998 |
| EP | 0 974 303 B2 | 7/2006 |
| EP | 2 767 826 A1 | 8/2014 |
| WO | WO 2000/031543 A1 | 6/2000 |
| WO | WO 2005/045416 A1 | 5/2005 |
| WO | WO 2007/012494 A1 | 2/2007 |
| WO | WO 2007/071562 A1 | 6/2007 |
| WO | WO 2009/118157 A1 | 10/2009 |
| WO | WO 2014/001382 A1 | 1/2014 |

OTHER PUBLICATIONS

West, Anthony R., Solid State Chemistry and Its Applications, Wiley, New York, 1988, 358.*
Shestopalov, et al, Nitrile cyclization reactions. 50. Regioselectivity of reactions of quaternized pyridin-3-ylidene derivatives of malononitrile and cyanoacetic ester with 1,3-dicarbonyl compounds. Crystal structure of 2-amino-3,5-dicarboethoxy-6-methyl-4-(1-methylpyridinio-3-yl)-4H-pyran iodide, Khimiya Geterotsiklicheskikh Soedinenii (2), 20.*
Habermüller, Katja et al., Electron-transfer mechanisms in amperometric biosensors, Fresenius Journal of Analytical Chemistry, 2000, pp. 560-568, vol. 366. 9 pages.
Heller, Adam and Feldman, Ben, Electrochemical Glucose Sensors and Their Applications in Diabetes Management, Chemical Reviews, 2008, pp. 2482-2505, vol. 108. 24 pages.
Hoenes, Joachim et al., The Technology Behind Glucose Meters: Test Strips, Diabetes Technology & Therapeutics, 2008, pp. S-10-S-26, vol. 10, Supplement 1. 18 pages.
International Search Report dated Jun. 22, 2016 in Application No. PCT/EP2015/069393. 6 pages.
Vering T et al: "A potentiostatic multi-pulse method using redox polymers for potentiometric measurements of enzymatic redox-reactions", Journal of Electroanalytical Chemistry and Interfacial Electrochemistry, Elsevier, Amsterdam, NL, vol. 364, No. 1-2, Jan. 31, 1994, pp. 277-279.

* cited by examiner

*Primary Examiner* — Erich A Leeser
(74) *Attorney, Agent, or Firm* — Woodard, Emhardt, Moriarty, McNett & Henry LLP

(57) ABSTRACT

The present invention relates to a chemical compound or a salt or solvate thereof being a phenazine-, phenanthridine-, phenanthroline-, quinoline-, quinoxaline-, acridine-isoquinoline-, pyrazine- or pyridine-derivative comprising a conjugated π-system and a π-acceptor group, and to uses thereof. The present invention further relates to a chemistry matrix and to a test element comprising the chemical compound of the present invention. The present invention also relates to a method of determining the amount of an analyte in a test sample, comprising contacting said test sample with a chemical compound, with a chemistry matrix, or with a test element of the invention and estimating the amount of redox equivalents liberated or consumed by the chemical compound, by the chemical compound comprised in said chemistry matrix, or by the chemical compound comprised in said test element, in the presence of said test sample, thereby determining the amount of an analyte in said test sample. Moreover, the present invention relates to a system comprising a test element according to the present invention and a device comprising a sensor for measuring the amount of redox equivalents liberated or consumed.

25 Claims, 6 Drawing Sheets

REDOXINDICATORS

FIELD OF THE INVENTION

Figure 1:
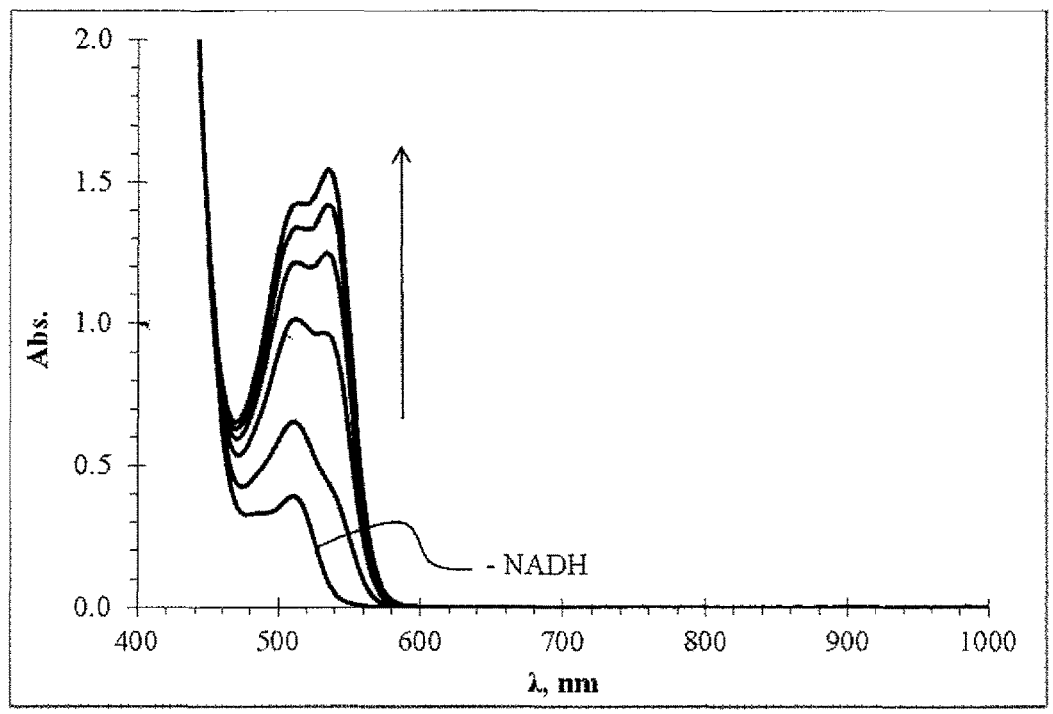

The present invention relates to a chemical compound or a salt or solvate thereof being a phenazine-, phenanthridine-, phenanthroline-, quinoline-, quinoxaline-, acridine-isoquinoline-, pyrazine- or pyridine-derivative comprising a conjugated π-system and a π-acceptor group, and to uses thereof. The present invention further relates to a chemistry matrix and to a test element comprising the chemical compound of the present invention. The present invention also relates to a method of determining the amount of an analyte in a test sample, comprising contacting said test sample with a chemical compound, with a chemistry matrix, or with a test element of the invention and estimating the amount of redox equivalents liberated or consumed by the chemical compound, by the chemical compound comprised in said chemistry matrix, or by the chemical compound comprised in said test element, in the presence of said test sample, thereby determining the amount of an analyte in said test sample. Moreover, the present invention relates to a system comprising a test element according to the present invention and a device comprising a sensor for measuring the amount of redox equivalents liberated or consumed.

RELATED ART

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Modern methods of analyte detection and measurement often rely on analyte-specific enzymes to confer specificity to the method. Frequently, redox enzymes are used, which either transfer redox equivalents to their substrate (reduction of substrate), or, more typically, withdraw redox equivalents from the substrate (oxidation of substrate). Most redox enzymes require the presence of a redox cofactor like, e.g., PQQ, NAD or FAD or the reduced forms thereof $PQQH_2$ NADH or FADH, from or to which redox equivalents are initially transferred by the enzyme. Redox equivalents withdrawn from an analyte may then be transferred, directly or indirectly, to a redoxindicator or to an electrode.

Generally, devices and methods known to the skilled person make use of test elements comprising one or more test chemistries, which, in presence of the analyte to be detected, are capable of performing one or more detectable detection reactions, such as optically or electrochemically detectable detection reactions. With regard to these test chemistries and methods related thereto, reference may be made e.g. to J. Hoenes et al. (The Technology Behind Glucose Meters: Test Strips, Diabetes Technology & Therapeutics, Volume 10, Supplement 1, 2008, S-10 to S-26, to US 2009/0246808 A1, and to Habermüller et al. (2000), Fresenius J Anal Chem 366:560). For electrochemical detection of glucose, a review is provided, e.g. in Heller & Feldman (2008), Chem. Rev. 108: 2482.

Redoxindicators are compounds which change their absorption upon undergoing a redox reaction (reviewed in, e.g., Naumann et al., "Indicator Dyes" in Ullmanns Encykl. Tech. Chem., 4. Aufl.; 1977, 13, 183-96; and in Hulanicki & Glab, "Redox Indicators: Characteristics and Applications" Pure & Appl. Chem., Vol. 50, 463-498; Pergamon Press Ltd., 1978). The majority of redoxindicators known in the art show a bathochromic shift, i.e. a change of spectral band position in the absorption, reflectance, transmittance, or emission spectrum to a longer wavelength, upon oxidation and there are only few examples of redox indicators showing a bathochromic shift upon reduction. Redox indicators showing a bathochromic shift upon reduction are particularly useful for colorimetric determination of an analyte.

A very well-known redoxindicator is phosphomolybdic acid (PMO). This compound, however has the disadvantage that the redox states are not very well defined (Burstein, S.; Anal. Chem.; 1953; 25 (3); 422-424; Rodrigues da Rocha, D.; Research Journal of Chemistry and Environment; 2007; 11; 102-103). Moreover, the reduced form of PMO has also only a low extinction coefficient and PMO is not reduced directly by a reduced coenzyme and, therefore a mediator has to be used.

Alternative chromogenic redoxindicators are described in EP 0 831 327. The drawback of the compounds described therein is the quite low extinction coefficient of the reduced form of these compounds. Furthermore, tetrazolium salts are used as redox indicators (see, e.g. EP 0 574 769), but these compounds are not very stable and also require the use of a mediator like phenazine methosulfate to work in context with dehydrogenases (Pacaud-Mercier, K. et al.; Bioorganic Chemistry; 35 (1); 2007; 59-67). Phenazine methosulfate, however, is easily reduced by ascorbate, which may cause interference.

Further proposed as redoxindicators were: resazurins, in which, however, the color difference between the oxidized and the reduced form is too small for many applications; heteropoly acids (like PMO)(see, e.g. EP 0 431 456), which, however, have a low molar extinction and an absorption maximum at a wavelength unsuited for many applications.

In WO 00/31543 A1, acridine-esters are disclosed, which can be reduced by NADH to form acridan-derivatives; since acridans, in contrast to acridines, cannot be induced to undergo the hydrogen peroxide induced chemiluminescence reaction disclosed, the chemiluminescence signal was found to be inversely proportional to the NADH concentration. Moreover, the signal generated is chemiluminescence, which requires specific detection equipment and a decreasing chemiluminescence signal is hard to measure. Moreover, U.S. Pat. No. 5,498,542 A discloses phenoxazines and phenothiazines as mediators in electrochemical determination of glucose. The compounds disclosed comprise quinoid systems, in which the π-electron system is known to be shortened upon reduction; accordingly, the compounds of U.S. Pat. No. 5,498,542 A undergo a hypsochromic shift upon reduction, which is difficult to measure.

Thus, there is a need in the art to provide redoxindicators, in particular redoxindicators avoiding the problem described above.

Problem to be Solved

It is therefore an objective of the present invention to provide compounds, means and methods to comply with the aforementioned needs, avoiding at least in part the disadvantages of the prior art.

SUMMARY OF THE INVENTION

This problem is solved by a chemical compound or a salt or solvate thereof comprising the structure as disclosed herein, by a chemistry matrix comprising said chemical compound or salt or solvate thereof, by a test element comprising said chemical compound or salt or solvate thereof, and by the method for determining the amount of an analyte as disclosed herein. Further embodiments, which might be realized in an isolated fashion or in any arbitrary combination are listed in the dependent claims and are described in this specification.

Accordingly, the present invention relates to a tricyclic chemical compound or a salt or solvate thereof, said tricyclic chemical compound comprising a tricyclic heterocyclic group covalently bound to a π-acceptor group having the general structure of formula (I)

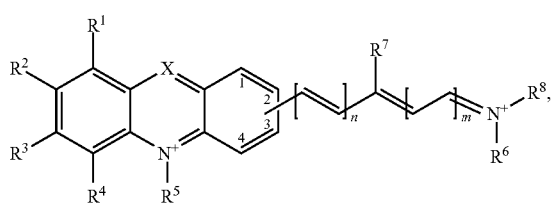

wherein

X is —CH— or —N—, $R^1$, $R^2$, $R^3$, $R^4$ are independently selected from hydrogen; alkyl, in an embodiment, lower alkyl; unsubstituted or substituted aryl, in an embodiment, $ArR^9$ or phenyl; halide; nitro; sulfonate; —CN; —COOH; —$OR^9$; —$SR^9$; —$SSR^9$; —$C(O)OR^9$; —$C(O)NHR^9$; $NHC(O)R^9$; $C(O)NH2$;

with $R^9$ selected from alkyl, in an embodiment, lower alkyl; or unsubstituted or substituted aryl, in an embodiment, phenyl;

and/or wherein $R^a$ and $R^{a+1}$, with a=1, 2, or 3, together form a bridge to form a 5- to 6-membered cycloalkyl, aryl, heterocycloalkyl or heteroaryl ring, in an embodiment, form a —CH=CH—CH=CH— bridge; in an embodiment, said heterocycloalkyl or heteroaryl ring comprises at least one heteroatom selected from O, N, or S; in a further embodiment, said heterocycloalkyl or heteroaryl ring comprises only one heteroatom selected from O, N, or S.

$R^5$ and $R^6$ are independently selected organic side chains, in an embodiment, methyl, in a further embodiment, ethyl, in a further embodiment, phenyl, n is an integer between 0 and 5, in an embodiment 0, 1, or 2, m is an integer selected from 0 and 1, $R^7$ is H or an organic side chain, $R^8$ is an organic side chain, or wherein $R^8$ and $R^7$ together form a bridge to form a 5- to 6-membered, optionally substituted, heterocycloalkyl or heteroaryl ring.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

In an embodiment, a chemical compound comprising a structure as specified herein is derivable from a compound consisting of said formula by at most three chemical modification reactions, in a further embodiment, by at most two modification reactions, in a further embodiment, by at most one modification reaction. The term "chemical modification reaction" is known to the skilled person and relates to a chemical reaction modifying the chemical structure of a chemical compound according to the present invention, in an embodiment, without changing its characteristic structural features. Thus, in an embodiment, the term chemical modification reaction relates to a modification of a side chain of the chemical compound of the present invention. In an embodiment, modification of a side chain is alkylation, e.g. methylation or ethylation, acylation, in a further embodiment, acetylation, glycosylation, hydroxylation, hydroxyalkylation, or any combination thereof. In an embodiment, the modified chemical compound has the same or a similar activity with regard to the applications referred to herein as the parent chemical compound as described herein. In an embodiment, the compound according to the invention is modified in such a manner that it is soluble in aqueous buffered solution, in an embodiment in 50 mM sodium phosphate buffer pH 7 at a temperature of 25° C. In an embodiment, said solubility is >15 mmol/L, in a further embodiment >30 mmol/L, in a further embodiment >50 mmol/L. Substituents which increase hydrophilicity and/or solubility are well known in the art. Further examples are hydroxyl, carboxyl, sulfonic acid, phosphate and phosphonate substituents.

Further, as used in the following, the terms "preferably", "more preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

As used herein, the terms "chemical compound", "salt", and "solvate" are used in their usual meaning known to the skilled chemist. If the net charge of a compound according to the present invention is positive, exemplary counter ions are trifluoromethanesulfonate (triflate), sulfate, alkyl sulfonate, tosylate, phosphate, tetrafluoroborate, hexafluorophosphate trifluoracetate, perchlorate, chloride or nitrate ions. If the net charge of a compound according to the present invention is negative, exemplary counterions are lithium, sodium, and/or potassium ions, or tetramethlyammonium ions. In an embodiment, the net charge of a compound according to the present invention is the net charge of the compound in aqueous solution under standard conditions of 25° C., $10^8$ Pa, and pH=7. As will be appreciated from the structural definitions provided herein, the term "tricyclic chemical compound" relates to a compound comprising a tricyclic structure as specified herein, which, in an embodiment, does not exclude that the tricyclic chemical compound comprises further cyclic structures.

The term "side chain" is understood by the skilled person and relates to an atom or chemical group attached covalently to the core part of a chemical compound as described herein, said core part also being referred to as "main chain" or "backbone". In an embodiment, the side chain is an organic side chain as described herein below. The term "substituted" side chain relates to a side chain substituted at one or more positions, in an embodiment, at 1, 2, or 3 positions, wherein substituents may be attached at any available atom to produce a stable chemical compound. It is understood by the skilled person that the term "optionally substituted" side chain relates to an unsubstituted or to a substituted side chain.

The term "organic side chain", as used herein, relates to any, optionally substituted, side chain comprising at least one carbon atom. In an embodiment, the organic side chain is an, optionally substituted, alkyl, alkenyl, alkinyl, aryl, aralkyl, cycloalkyl, heterocycloalkyl, or heteroaryl side chain. In an embodiment, a substituted organic side chain is an organic side chain substituted with at least one substituent independently selected from —COO$^-$, =O, —OH, —CN, halogen, —NH$_2$, —NH(alkyl), —N(alkyl)$_2$, —N(alkyl)$_3^+$, —NH(aryl), N(aryl)$_2$, —NO$_2$, —O(alkyl), —O—(CH$_2$)$_n$—OH, —O—(CH$_2$)n-O(alkyl), —O(aralkyl), —O(aryl), —OPO$_3^{2-}$, —PO$_3^{2-}$, —OSO$_3^-$ and —SO$_3^-$. In an embodiment, the alkyl, aryl, and aralkyl groups of the substituents are not further substituted by groups comprising alkyl, alkenyl, alkinyl, aryl, aralkyl, heterocycloalkyl, or heteroaryl groups. In a further embodiment, the alkyl, aryl, and aralkyl groups of the substituents are not further substituted.

The term "alkyl", as used herein, relates to a straight or branched chain, saturated hydrocarbon group, linked to the main chain by a covalent bond to at least one of its at least one carbon atoms. Further alkyl groups are straight chain alkyls, e.g., in an embodiment, methyl, ethyl, propyl, butyl, pentyl, hexyl, heptyl, octyl, nonyl, decyl, undecyl, dodecyl, or branched chain alkyl groups, e.g., —CH(CH$_3$)$_2$, —CH(CH$_2$CH$_3$)$_2$, —C(CH$_3$)$_3$, —C(CH$_2$CH$_3$)$_3$, —CH(CH$_3$)(CH$_2$CH$_3$), —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, or —CH(CH$_3$)CH(CH$_3$)CH(CH$_3$)$_2$. Accordingly, alkyl groups include primary alkyl groups, secondary alkyl groups, and tertiary alkyl groups. Further envisaged alkyl groups are lower alkyl groups, i.e. in an embodiment, alkyl groups with at most 12 carbon atoms, in a further embodiment with at most 9 carbon atoms, in a further embodiment with at most 5 carbon atoms. The term "cycloalkyl" relates to a circularly closed, saturated or unsaturated hydrocarbon group, in an embodiment, with 3 to 12 carbon atoms. Further envisaged as cycloalkyls are cyclopropyl, cyclobutyl, cyclopentyl, cyclohexyl, cycloheptyl, and cyclooctyl.

The term "alkenyl" side chain relates to a side chain comprising at least one C=C double bond and linked to the main chain by a covalent bond to at least one of its at least two carbon atoms. Accordingly, the term "alkinyl" side chain relates to a side chain comprising at least one C≡C triple bond linked to the main chain by a covalent bond to at least one of its at least two carbon atoms.

The term "cycloalkenyl" relates to a circularly closed hydrocarbon group, in an embodiment, with 5 to 12 carbon atoms, comprising at least one C=C double bond and linked to the main chain by a covalent bond to at least one of its at least two carbon atoms. The term "cycloalkinyl" relates to a circularly closed hydrocarbon group, in an embodiment, with 8 to 12 carbon atoms, comprising at least one C≡C triple bond and linked to the main chain by a covalent bond to at least one of its at least two carbon atoms.

As used herein, the term "alkoxy" side chain relates to an —O-alkyl side chain, in an embodiment, having the indicated number of carbon atoms. In an embodiment, the alkoxy side chain is —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, or —O-neohexyl. In an embodiment, the alkoxy side chain is —O-methyl or —O-ethyl.

The term "aryl", as used herein, relates to an aromatic ring or ring system having 6 to 14 carbon atoms, in an embodiment, comprising one, two, or three aromatic rings. Further evisaged aryl side chains are phenyl, naphthyl, anthracenyl, and phenanthrenyl. The term "ring", in the context of the chemical compounds of the present invention, is understood by the skilled person; accordingly, the term "ring system" relates to a chemical structure comprising at least two rings sharing at least one covalent bond. Thus, in an embodiment, "aryl" also includes aromatic ring systems fused with a cycloalkyl and/or a heterocycloalkyl ring.

As used herein, the term "aralkyl" relates to an alkyl side chain, wherein at least one hydrogen is replaced by an aryl side chain. In an embodiment, aralkyl is benzyl or phenethyl.

The term "heterocycloalkyl", as used herein, relates to a saturated or partially unsaturated ring or ring system having 5 to 14 ring atoms, in an embodiment, 5 to 7 ring atoms, wherein at least one ring atom is a heteroatom selected from the group consisting of N, O, and S, said ring or ring system being linked to the main chain by a covalent bond to a C or N atom of said ring or ring system. In an embodiment, heterocycloalkyl is azepinyl, dihydrofuryl, dihydropyranyl, imidazolidinyl, imidazolinyl, isothiazolidinyl, isoxazolidinyl, morpholinyl, oxazolidinyl, piperazinyl, piperidinyl, pyrazolidinyl, pyrrolidinyl, tetrahydrofuryl, tetrahydropyranyl, thiadiazolylidinyl, thiazolidinyl, or thiomorpholinyl.

As used herein, the term "heteroaryl" relates to an aromatic ring or ring system having 5 to 14 ring atoms, in an embodiment, 5 to 7 ring atoms, wherein at least one ring atom is a heteroatom selected from the group consisting of N, O, and S, said ring or ring system being linked to the main chain by a covalent bond to a C or N atom of said ring or ring system. In an embodiment, up to 4, in a further embodiment, up to 3, in a further embodiment, up to 2 ring atoms per ring are heteroatoms independently selected from the group of heteroatoms consisting of N, O, and S. In an embodiment, heteroaryl is pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, or indolyl.

In the context of the structural formulas of the present specification, "X" relates to a group —CH— or to a nitrogen atom (N); further, n is an integer between 0 and 5, in an embodiment, 0, 1, or 2, and m is an integer selected from 0 and 1. In an embodiment, m is 0. Also in an embodiment, the sum of n and m, in an embodiment is 3 or less, in a further embodiment the sum of n and m is 2 or less; in a further embodiment, the sum of n and m is 1.

Further, in the context of the structural formulas of the present specification, side chains $R^1$, $R^2$, $R^3$, $R^4$ are independently selected from hydrogen; alkyl, in an embodiment, lower alkyl; unsubstituted or substituted aryl, in an embodiment, ArR⁹ or phenyl; halide; nitro; fonate; —CN; —COOH; —OR⁹; —SR⁹; —SSR⁹; —C(O)OR⁹; —C(O)NHR⁹; NHC(O)R⁹; —C(O)NH₂; with R⁹ selected from alkyl, in an embodiment, lower alkyl; or unsubstituted or substituted aryl, in an embodiment, phenyl. In an embodiment, $R^a$ and $R^{a+1}$, with a=1, 2, or 3, together form a bridge to form a 5- to 6-membered cycloalkyl, aryl, heterocycloalkyl or heteroaryl ring. Thus, in an embodiment, $R^1$ and $R^2$ together form a bridge to form a 5- to 6-membered cycloalkyl, aryl, heterocycloalkyl or heteroaryl ring, $R^2$ and $R^3$ together form a bridge to form a 5- to 6-membered cycloalkyl, aryl, heterocycloalkyl or heteroaryl ring, and/or $R^3$ and $R^4$ together form a bridge to form a 5- to 6-membered cycloalkyl, aryl, heterocycloalkyl or heteroaryl ring. In a further embodiment, $R^a$ and $R^{a+1}$, with a=1, 2, or 3, together form a —CH=CH—CH=CH— bridge. Thus, in an embodiment, $R^1$ and $R^2$ together form a —CH=CH—CH=CH— bridge, or $R^2$ and $R^3$ together form a —CH=CH—CH=CH— bridge, or $R^3$ and $R^4$ together form a —CH=CH—CH=CH— bridge, or both $R^1/R^2$ and $R^3/R^4$, respectively, together form a —CH=CH—CH=CH— bridge. In an embodiment, at least one of $R^1$, $R^2$, $R^3$, and $R^4$ is hydrogen. In a further embodiment, at least two or at least three of $R^1$, $R^2$, $R^3$, and $R^4$ are hydrogen. In a further embodiment, $R^1$, $R^2$, $R^3$, and $R^4$ are hydrogen.

Moreover, side chains $R^5$ and $R^6$ are independently selected organic side chains, in an embodiment, optionally substituted aryl, alkyl or cycloalkyl, in a further embodiment, methyl, propyl, butyl, cyclopentyl, or cyclohexyl, in a further embodiment, ethyl, in a still further embodiment, phenyl or (C3-C6)alkylsulfonate or (C3-C6)alkyl-N⁺Me₃; side chain $R^7$ is H or an organic side chain, $R^8$ is an organic side chain. It is, however also envisaged that $R^8$ and $R^7$ together form a bridge to form a 5- to 6-membered heterocycloalkyl or heteroaryl ring.

It is understood by the skilled person that the side chain comprising the π-acceptor group may be covalently linked to the ring system of formula (I) via any of carbon atoms C1 to C4 indicated in formula (I). Side chain π-acceptor group, in an embodiment, is covalently connected to the heterocyclic group directly or via one or more carbon-carbon double bonds (or vinylene group), wherein in case side chain π-acceptor group is covalently connected to the heterocyclic group via more than one carbon-carbon double bonds, the more than one carbon-carbon double bonds are conjugated (not isolated or cumulated) Further embodiments of attachment of the π-acceptor group are specified elsewhere herein.

In an embodiment, in the tricyclic chemical compound, X is —N— and the π-system is covalently bonded to C1, C2, C3, or C4 of the heteroaromatic system as indicated in formula (I); or X is —CH— and the π-system is covalently bonded to C2 or C4 of the heteroaromatic system as indicated in formula (I). In a further embodiment, in the tricyclic chemical compound, X is —N— and the π-system is covalently bonded to C1 of the heteroaromatic system as indicated in formula (I); or X is —CH— and the π-system is covalently bonded to C2 of the heteroaromatic system as indicated in formula (I).

π-Acceptor groups of compounds according to the invention compromise a bivalent quaternary nitrogen-containing cationic group, i.e. an iminium group (=N⁺R₂). In an embodiment, the π-acceptor group is not reduced by reduced coenyzmes NADH, FADH; or PQQH. In an embodiment, $R^7$ and $R^8$ together form an, optionally substituted, heterocycloalkyl, heteroaryl, heterocyclyl, or heterocycloalkylcyclic group, in an embodiment, e.g., 3H-indolyl, 3,3-dimethyl-3H-indolyl, 1-methyl-1H-benzimidazolyl, benzoxazolyl, benzothiazolyl, benzoselenazolyl, benz[cd]indolyl, or pyridyl. More π-acceptor groups are well known in the art and used in polymethine dye chemistry, e.g. from A. I. Tolmachev, A. Y. Il'chenko, in Kirk-Othmer Encyclopedia of Chemical Technology, John Wiley & Sons, Inc., 2000, and from further references cited herein below.

In an embodiment, the π-acceptor group is selected from the group consisting of (i) a side chain comprising the structure of formula (II)

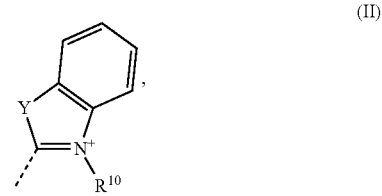

wherein Y is —N(Me)-, —S—, —Se—, —O—, or —C(Me)₂-, (ii) a side chain comprising the structure of formula (III)

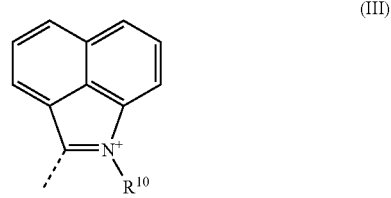

(iii) a side chain comprising the structure of formula (IV)

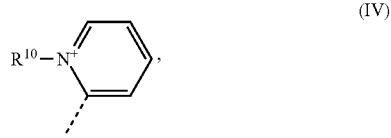

and (iv) a side chain comprising the structure of formula (V)

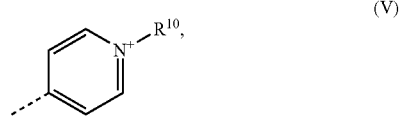

wherein in each of formulas (II) to (V), $R^{10}$ is alkyl or cycloalkyl, in an embodiment methyl.

In a further embodiment, the tricyclic chemical compound is 10-methyl-1-[(E)-2-(1,3,3-trimethyl-3H-indolium-2-yl)vinyl]phenazinium (formula XX) or the tricyclic chemical compound is 9-ethoxy-10-methyl-1-[(E)-2-(1,3,3-trimethyl-3H-indolium-2-yl)vinyl]phenazinium (formula XXI). The counter ions shown in these formulas are only exemplary counterions and can be exchanged to any other suitable counter ions as mentioned above.

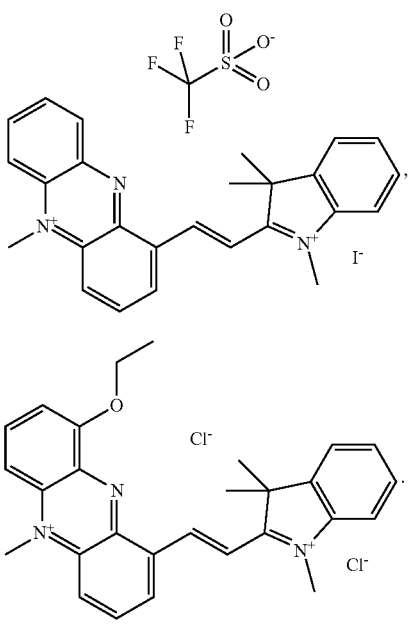

(XX)

(XXI)

In an embodiment, the chemical compound of the present invention is a compound having a midpoint potential of at least −0.4 V under standard conditions and versus a standard hydrogen electrode. In a further embodiment, the chemical compound of the present invention is a compound having a midpoint potential of at least −0.1 V, in a further embodiment, at least 0.2 V under standard conditions and versus a standard hydrogen electrode. In an embodiment, reduction as used in the context with the compounds of the present invention relates to acquisition of two electrons by the ring system according to the following scheme:

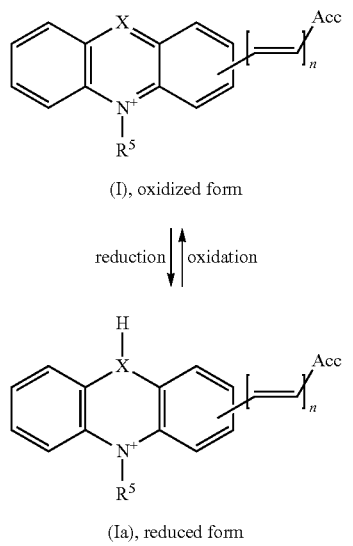

In the above figures, Acc represents a π-acceptor group as detailed above.

Accordingly, in the compounds of the present invention, a polymethine type donor-acceptor dye is formed upon reduction. Thus, in an embodiment, the chemical compound of the present invention is a compound undergoing a bathochromic shift upon reduction. In a further embodiment, the reduced form of said chemical compound has an absorption maximum at a wavelength of 400 to 800 nm.

Advantageously, it was found in the work underlying the present invention, that the chemical compounds described herein are compounds undergoing a bathochromic shift upon reduction and that the redox potential of said compounds makes them suited for receiving redox equivalents in particular from reduced nicotine adenine dinucleotide (NADH). Moreover, it was found that said compounds have at least one absorption maximum in the range of visible light, enabling visual inspection and/or photometric determination of their redox state at a wavelength where interference from other compounds comprised, e.g. in blood samples, is minimal or at least acceptable. Some of the compounds also are fluorogenic upon reduction and, therefore, can be used for determining or detecting reducing agents by fluorescence spectroscopy or fluorescence imaging (see, e.g., R. Freeman, R. Gill, I. Shweky, M. Kotler, U. Banin, I. Willner, Angewandte Chemie 2009, 121, 315-319).

The definitions made above apply mutatis mutandis to the following. Additional definitions and explanations made further below also apply for all embodiments described in this specification mutatis mutandis.

Further, the present invention relates to a chemistry matrix comprising a redox cofactor and a chemical compound or a salt or solvate thereof, said chemical compound comprising a heterocyclic group (Het) covalently bound to a π-acceptor group (Acc), having the general structure of formula (VI)

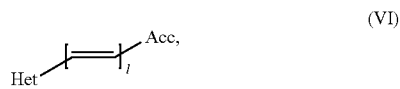

wherein Het comprises a structure selected from formulas (VII) to (XV):

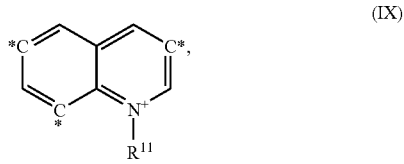

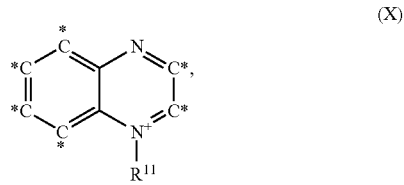

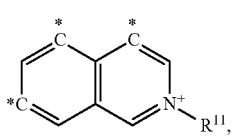 (XI)

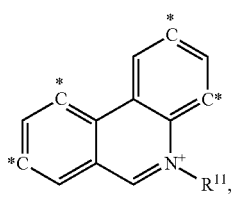 (XII)

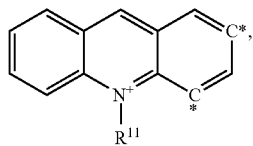 (XIII)

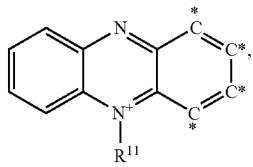 (XIV)

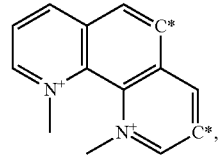 (XV)

and, in an embodiment,

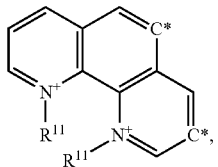 (XVa)

wherein $R^{11}$ is an organic side chain, in an embodiment, methyl, in a further embodiment, ethyl, in a further embodiment, phenyl, wherein the -(vinylene)$_l$Acc group is attached to one of the carbon atoms indicated as C*, wherein l is an integer between 0 and 5, in an embodiment, 0, 1, or 2, and wherein Acc is selected from —(C=O)Aryl, —(C=C(CN)$_2$), and a π-acceptor group of the general formula (XVI)

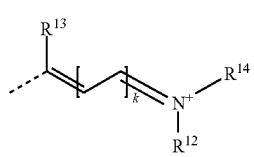 (XVI)

wherein $R^{12}$ is an organic side chain, in an embodiment, methyl, in a further embodiment, ethyl, in a further embodiment, phenyl, k is an integer selected from 0 and 1, $R^{13}$ is H or an organic side chain, $R^{14}$ is an organic side chain, or wherein $R^{13}$ and $R^{14}$ together form a bridge to form a 5- to 6-membered heterocycloalkyl or heteroaryl ring.

The term "chemistry matrix" is known to the skilled person and relates to a mixture of compounds comprising the aforesaid chemical compound and a redox cofactor as described herein below. In an embodiment, the chemistry matrix of the present invention, in addition to the compounds indicated above, further comprises an oxidoreductase as described herein below. It is understood by the skilled person that the composition may comprise additional components, e.g., in an embodiment, buffer components (e.g., of phosphate buffered saline, Tris buffer, citrate buffer, glycerine phosphate buffer, or Good's buffer) or other salts, detergents, or the like, including the components as specified herein below.

The term "redox cofactor" or "cofactor", as used herein, relates to a redox-active flavine, nicotinamide or pyrroloquinoline quinone (PQQ) coenzyme. The skilled person knows how to select one of the aforesaid coenzymes appropriately, depending on the oxidoreductase selected. In an embodiment, the flavine, nicotinamide or PQQ coenzyme is flavine adenine dinucleotide (FAD), flavine mononucleotide (FMN), or PQQ, or a derivative of one of the aforesaid compounds. In a further embodiment, the redox cofactor is nicotinamide adenine dinucleotide (NAD$^+$), nicotinamide adenine dinucleotide phosphate (NADP$^+$), or a derivative thereof. Further NAD$^+$ or NADP$^+$ derivatives are stabilized NAD$^+$ or NADP$^+$ derivatives, i.e. in an embodiment, carbacyclic derivatives, including, in a further embodiment, carbaNAD$^+$ or carbaNADP$^+$, as disclosed, e.g., in Slama (Biochemistry 27: 183 (1988)), Hutchinson et al. (Chem. Comm. 24: 2765 (1996)), U.S. Pat. No. 5,801,006, WO98/33936, WO01/49247 and WO2007/012494. In a further embodiment, the redox cofactor is reduced NAD$^+$, NADP$^+$, carbaNAD$^+$, or carbaNADP$^+$, i.e., in an embodiment, NADH, NADPH, carbaNADH, or carbaNADPH. As will be understood by the skilled person, the term "comprising a redox cofactor", in an embodiment, includes cases where at least one redox cofactor is added as such to a mixture of compounds, as well as cases where at least one redox cofactor is present in the chemistry matrix as a constituent of a different compound added to said mixture of compounds, e.g., in an embodiment, as a constituent of one or more cell(s) added to said mixture of compounds.

As used herein, the term "heterocyclic group" relates to a chemical side chain according to one of formulas (VII) to (XV), in an embodiment formulas (VII) to (XVa), as depicted above. In an embodiment, the heterocyclic group is a redox active heterocyclic group. Redox active heterocyclic groups are known from the prior art (J. W. Bunting, V. S. F. Chew, G. Chu, The Journal of Organic Chemistry 1982, 47, 2303-2307; D. Ostovic, I. S. H. Lee, R. M. G. Roberts, M. M. Kreevoy, The Journal of Organic Chemistry 1985, 50, 4206-4211; R. Hisada, T. Yagi, The Journal of Biochemistry 1977, 82, 1469-1473; J. W. Bunting, A. W. C. Ng, Bioorg Chem 1993, 21, 156-169.)

Side chain Acc, as used in the context of the formulas of the present invention and as specified above, is a π-acceptor group known to the skilled person, e.g., in an embodiment, from polymethine dye chemistry (see, e.g., A. I. Tolmachev, A. Y. Il'chenko, in Kirk-Othmer Encyclopedia of Chemical Technology, John Wiley & Sons, Inc., 2000). Side chain Acc, in an embodiment, is covalently connected to the heterocyclic group directly or via one or more ethenyl (vinyl) or ethenylene (vinylene) groups. In an embodiment the moiety XVI is substituted in such a manner that adjacent atoms of the conjugated π system including the iminium nitrogen atom and the venylene carbon atoms are linked by a chain of 3 or 4 carbon atoms or by a —CH2-O—CH2- chain. Such ring closures are well known in polymethine dye chemistry (see, e.g. A. V. Kulinich, N. A. Derevyanko, A. A. Ishchenko, Journal of Photochemistry and Photobiology A: Chemistry 2008, 198, 119-125; I. L. Mushkalko, Y. A. Sogulyaev, Ukr. Khim. Zh. (Russ. Ed.) 1986, 52, 509-513; A. Samanta, M. Vendrell, R. Das, Y.-T. Chang, Chem Commun (Camb) 2010, 46, 7406-7408; X. Chen, X. Peng, A. Cui, B. Wang, L. Wang, R. Zhang, Journal of Photochemistry and Photobiology A: Chemistry 2006, 181, 79-85.) In an embodiment, Acc is —(C=O)aryl, —(C=C (CN)$_2$) or a π-acceptor group of the general formula (XVI)

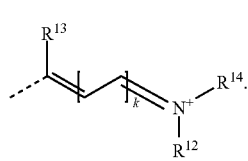

(XVI)

As used in the context of the structural formulas of the present specification, k relates to an integer selected from 0 and 1. In an embodiment, k is 0. Also in an embodiment, the sum of l and k, in an embodiment, is 3 or less, in a further embodiment, the sum of l and k is 2 or less; in a further embodiment, the sum of l and k is 1.

As used herein, $R^{12}$ relates to an organic side chain, in an embodiment, optionally substituted aryl, alkyl or cycloalkyl, in a further embodiment, methyl, propyl, butyl, cyclopentyl, or cyclohexyl, even in a further embodiment, ethyl, in a further embodiment, phenyl or (C3-C6)alkylsulfonate or (C3-C6)alkyl-N$^+$Me$_3$. $R^{13}$ is an organic side chain. In an embodiment, $R^{12}$ and $R^{13}$ together form a bridge to form an, optionally substituted, 5- to 6-membered heterocycloalkyl or heteroaryl ring.

According to the present invention, the side chain comprising the π-acceptor group is covalently linked to the ring system of redox active moiety via any of indicated carbon atoms C*. Further embodiments of attachment of the π-acceptor group are specified elsewhere herein.

In an embodiment, the chemical compound is a compound comprising or consisting of a structure selected from formulas (XVII) to (XXVII), (XXX) to (XXXII), and, in an embodiment, (LII):

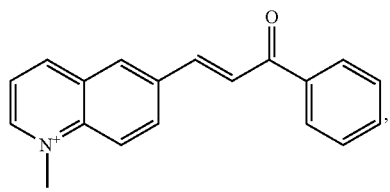

(XVII)

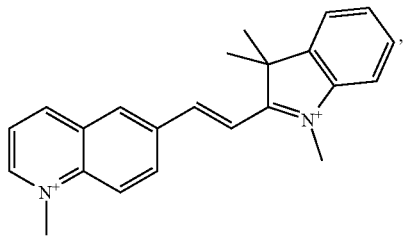

(XVIII)

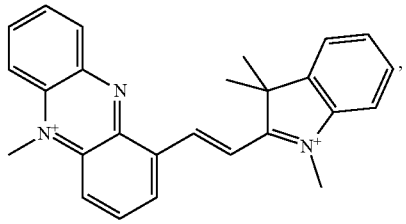

(XX)

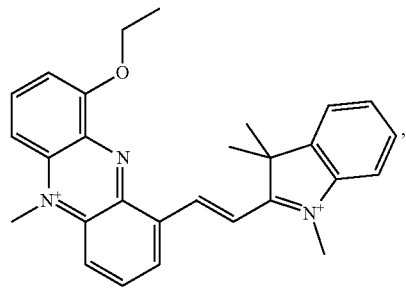

(XXI)

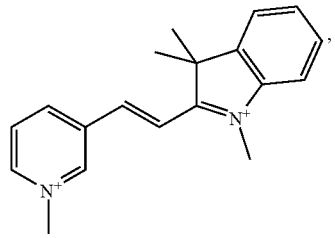

(XXIII)

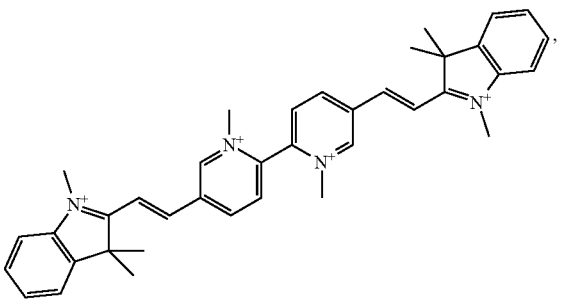

(XXIV)

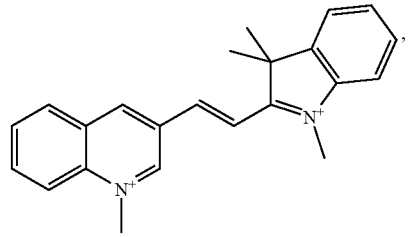

(XXV)

-continued

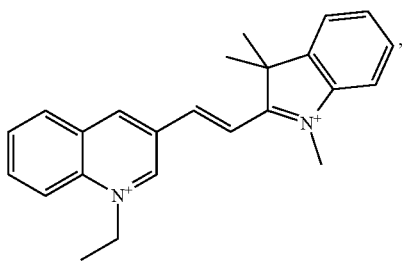
(XXVI)

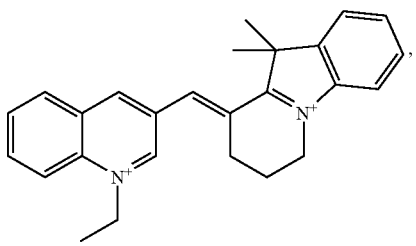
(XXVII)

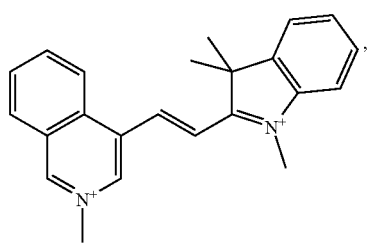
(XXX)

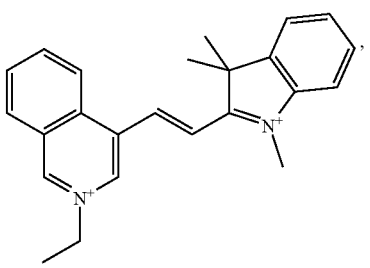
(XXXI)

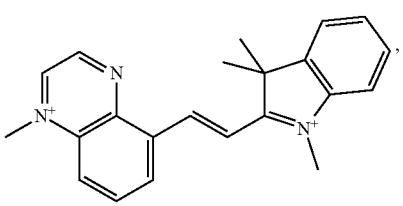
(XXXII)

and, in an embodiment,

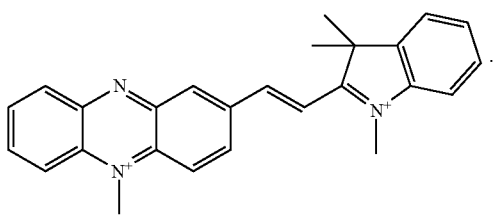
(LII)

A chemistry matrix according to the present invention can be provided, in an embodiment, by dissolving the components of the composition of the present invention first in a solvent or mixture of solvents. In a further embodiment, said solvent or mixture of solvents is subsequently removed by a suitable treatment such that the remaining composition is essentially free of the said solvent or solvent mixture. Suitable treatments to be in an embodiment envisaged by the present invention include heat treatment, evaporation techniques, freeze drying and the like. In an embodiment, the envisaged treatment is heat treatment and, in particular, heat treatment under the following conditions: heat treatment at about 60° C. or more for approximately 20 to 45 minutes or at about 95° C. for approximately 1 to 2 minutes with heat circulation; thickness of the chemistry matrix of 20 to 200 micrometers or less; at a pressure of 1 bar or 0.1 bar. Moreover, it will be understood that in order to keep the chemistry matrix under dry conditions, storage is, in an embodiment, carried out in the presence of a drying agent, i.e., a desiccant. Suitable drying agents, in an embodiment, encompass silica gel, zeolites, calcium carbonate or magnesium sulfate. The compounds according to the invention can also be polymerized or copolymerized or incorporated in a polymer to form redoxactive films.

The terms "oxidoreductase" and "oxidoreductase enzyme", as used herein, refer to a polypeptide which is capable of catalyzing the, in an embodiment, specific, oxidation or reduction of a substrate by transferring hydrides ($H^-$) as redox equivalents to or from a redox cofactor as referred to herein elsewhere. In an embodiment, the oxidoreductase is a dehydrogenase, i.e. a polypeptide which is capable of catalyzing the oxidation of a substrate by transferring hydrides ($H^-$) as redox equivalents to an acceptor molecule, in an embodiment, to a redox cofactor as referred to herein elsewhere. Dehydrogenases envisaged by the present invention are, in an embodiment, those which depend on a redox cofactor (or sometimes referred to as co-enzyme) such as pyrroloquinoline quinone (PQQ) or a derivative thereof, nicotinamide-adenine-dinucleotide (NAD) or a derivative thereof, or a flavine cofactor, such as flavin-adenine-dinucleotide (FAD) or flavine mononucleotide (FMN), or a derivative thereof. Further dehydrogenases are, in particular, lactate dehydrogenase (EC number 1.1.1.27 or 1.1.1.28), glucose dehydrogenases (see below), alcohol dehydrogenase (EC number 1.1.1.1 or 1.1.1.2), L-amino acid dehydrogenase (EC number 1.4.1.5), glycerol dehydrogenase (EC number 1.1.1.6), malate dehydrogenase (EC number 1.1.1.37), 3-hydroxybutyrate dehydrogenase (EC number 1.1.1.30), or sorbitol dehydrogenase (EC number 1.1.1.14).

In a further embodiment, said oxidoreductase is a glucose dehydrogenase. In a further embodiment, said glucose dehydrogenase is selected from the group consisting of: glucose dehydrogenase (EC number 1.1.1.47), quinoprotein glucose dehydrogenase (EC number 1.1.5.2), in particular, pyrroloquinoline quinone (PQQ)-dependent glucose dehydrogenase (EC number 1.1.5.2), glucose-6-phospate dehydrogenase (EC number 1.1.1.49), nicotinamide adenine dinucleotide (NAD)-dependent glucose dehydrogenase (EC number 1.1.1.119) and flavin adenine dinucleotide (FAD)-dependent glucose dehydrogenase (EC number 1.1.99.10) or enzymatically active mutants thereof.

Enzymatically active mutants of the aforementioned enzymes can be obtained by substituting, adding or deleting one or more amino acids from the amino acid sequences reported for the aforementioned wild type enzymes in the prior art as recited before. Further envisaged as mutants are the mutants of the PQQ-dependent glucose dehydrogenase having an improved substrate specificity compared to their wild type counterparts as disclosed in U.S. Pat. No. 7,132, 270 or U.S. Pat. No. 7,547,535. Both documents are herewith incorporated by reference with respect to the mutants. Further mutants are those disclosed in Baik et al (Baik, Appl Environ Microbiol (2005) 71: 3285), Vasquez-Figuera et al. (Vasquez-Figuera, Chem BioChem (2007) 8: 2295), and WO 2005/045016.

Further envisaged in accordance with the present invention is a glucose dehydrogenase (E.C. 1.1.1.47) mutant disclosed in WO2009/103540A1 (p. 21) or EP1660648, having a mutation at least at amino acid positions 96, 170 and/or 252, herewith incorporated by reference. Further mutations envisaged at these amino acid positions are substitutions of Glu96Gly, Glu170Arg or Lys and/or Lys252Leu, e.g. the combination Glu170Lys/Lys252Leu. In a further embodiment, said mutations are mutations Glu170Arg and Gln252Leu in glucose dehydrogenase from *Bacillus subtilis*.

As will be realized by the skilled person, the chemical compounds according to the present invention can be used as reporter dyes in cases where an oxidoreductase is used as a reporter enzyme, in an embodiment, e.g. in an immunoassay or in an enzymatic determination of an analyte. Moreover, the chemical compounds can be used as substitute of tetrazolium salts for cell viability testing, with the benefit of higher extinction coefficients. Moreover, if the chemical compounds are modified, they can be used as a labelling reagent.

The term "redox equivalents" as used herein relates to the concept commonly used in redox chemistry well known to the skilled person. In an embodiment, the term relates to electrons which are transferred from a substrate of the oxidoreductase to the redox cofactor, and/or from said redox cofactor to a redox mediator, and/or from said redox mediator to and indicator compound and/or to an electrode.

In a further embodiment of the chemistry matrix of the present invention, said composition further comprises at least one detergent, swelling agent, film-forming agent, and/or solid particle. Suitable stabilizers, detergents, swelling agents, film forming agents, oxidizing agents, and/or solid particles to be used in the composition of the invention are known to the skilled artisan. In an embodiment, the said at least one detergent is selected from the group consisting of: sodium-N-methyl-N-oleoyltaurat, N-octanoyl-N-methyl-glucamid, Mega 8 (N-methyl-N-octanoylglucamide), dioctylsodium sulfosuccinate (DONS), Rhodapex® (in an embodiment CO-433 or CO-436). In an embodiment, said at least one swelling agent is selected from the group consisting of: methyl vinyl ether maleic acid anhydride copolymer, xanthan gum and methyl vinyl ether maleic acid copolymer. In an embodiment, said at least one film-forming agent is selected from the group consisting of: polyvinylpropionate dispersions, polyvinyl esters, polyvinyl acetates, polyacrylic esters, polymethacrylic acid, polyvinyl amides, polyamides, polystyrene and mixed polymerisates are also suitable such as of butadiene, styrene or maleic acid ester. In an embodiment, said at least one solid particle is selected from the group consisting of: silica particles, in particular, silicon dioxide, sodium silicates or aluminum silicates, kieselguhr, metal oxides, in particular, titan oxide and/or aluminum oxide, synthetic oxide materials, in particular, nanoparticles of oxide materials such as nanoparticles of silicon dioxide, aluminum oxide, or titan oxide, Kaolin, powder glass, amorphous silica, calcium sulfate, and barium sulfate.

Also, the present invention relates to a test element comprising a chemical compound and/or a chemistry matrix of the present invention.

The term "test element", as used herein, relates to a unit comprising a test chemistry, in an embodiment a dry test chemistry, on a solid support. In an embodiment, the test chemistry is comprised in a test field as described herein below. Also in an embodiment, the test element further comprises a capillary element, adapted for taking up and/or transporting a liquid by capillary action, in an embodiment, to a test field. In an embodiment, the test element is selected from an optical test element and an electrochemical test element. The test element may further optionally comprise at least one puncture element, such as a lancing element, which, in an embodiment, may be mounted movably with regard to the test field, in order to perform a puncture motion, a sampling motion or a lancing motion, thereby generating an incision in a skin surface. In an embodiment, the test field remains in a fixed position during the puncture, sampling or lancing motion, wherein a sample of a body fluid is transferred onto the test field, such as by a capillary action and/or by pressing the puncture element or a part thereof onto the test field after the puncture, sampling or lancing motion. In an embodiment, the test element is a test strip, a test tape, or a test disc.

The term "test field" relates to a continuous or discontinuous amount of test chemistry, which, in an embodiment, is held by at least one carrier, such as by at least one carrier film. Thus, the test chemistry may form or may be comprised in one or more films or layers of the test field, and/or the test field may comprise a layer setup having one or more layers, wherein at least one of the layers comprises the test chemistry. Thus, the test field may comprise a layer setup disposed on a carrier, wherein a sample of a body fluid may be applied to the layer setup from at least one application side, such as from an edge of the test field and/or from an application surface of the test field. In an embodiment, the test field has a multilayer setup, the multilayer setup comprising at least one detection layer having the at least one test material and further comprising at least one separation layer adapted for separating off at least one particulate component contained in the body fluid, wherein the separation layer is located between the detection layer and the capillary element. It is understood by the skilled person that all layers present optionally between the body fluid and the test field are selected as to allow passage of at least the analyte.

In an embodiment, the test element is an optical test element, i.e. a test element adapted to change at least one optical property in the presence of the analyte. In a further embodiment, at least one chemistry matrix comprised in the test element performs at least one optically detectable detection reaction in the presence of the analyte. Also in an embodiment, the detection reaction is a redox reaction. In a further embodiment, the detection reaction produces redox equivalents and/or electrons as intermediates and/or products. In an embodiment, the optically detectable signal produced by the detection reaction is proportional to the amount and/or to the concentration of the analyte in the sample.

In an embodiment, in the test element adapted to change at least one optical property in the presence of an analyte, in an embodiment, the compound of the present invention changes at least one optical property in the presence of an analyte. It is, however, also envisaged that the test element additionally comprises an indicator reagent. The term "indicator reagent", as used herein, in an embodiment, relates to a compound changing at least one optical property dependent on, in an embodiment, proportional to, the redox state of the chemical compound of the present invention comprised in the test element. In an embodiment, the indicator reagent is an optical indicator substance, which performs at least one optically detectable property change when the chemical compound of the present invention comprised in the chemistry matrix changes its redox state in the presence of the analyte. Thus, the at least one indicator reagent, in an embodiment, comprises one or more dyes performing a change in an optical property indicative of the enzymatic reaction of the at least one enzyme and the analyte.

The term "optical property", as used herein, relates to a property which can be detected by an optical instrument. Specifically, the optical property may be or may comprise at least one property selected from the group consisting of: a reflection property, a transmission property, an emission property, a scattering property, a fluorescence property, a phosphorescence property, a diffraction property, and a polarization property. In an embodiment, an optical property as referred to herein refers to a property of a chemical compound which can be optically detected such as light absorption, light emission, light remission, or properties associated therewith. It will be understood that such a change of at least one optical property as used herein encompasses the detection of the presence of a property which was not detectable before, the detection of the absence of a property which has been detected before, and the detection of quantitative changes of a property, i.e., the detection of the change of the signal strength which correlates to the extent of the change of the at least one optical property. Further optical properties envisaged by the present invention are color, fluorescence, luminescence, or refractometry. Methods of converting the optical property as defined above into a physical signal which can be read as a measurement value are well known in the art and are described, e.g., in EP 0 821 234, EP 0 974 303, and US 2005/0023152.

The optical property of the chemical compound and/or of an indicator reagent, according to the present invention, changes dependent on the activity of the enzyme of the present invention. Thus, in an embodiment, the change of the optical property only occurs if the enzyme catalyzes the detection reaction. In a further embodiment, the change of optical property is proportional to the number of catalytic cycles undergone by the enzyme present in the chemistry matrix. Thus, in a further embodiment, the change of optical property is proportional to the number of analyte molecules converted by the enzyme.

Also in an embodiment, the test element is an electrochemical test element and the chemical compound of the present invention has the function of being a redox mediator, in an embodiment mediating transfer of redox equivalents between a redox cofactor and an electrode of the test element.

Accordingly, the test element, in an embodiment, comprises at least two electrodes contacting, directly or indirectly, the chemistry matrix, as specified elsewhere herein. Suitable electrodes, electrode setups, and modes of operation are known to the skilled person and are described, e.g. in WO 2007/071562 A1, WO 2014/001382 A1, US 2005/0023152 and references cited therein. Moreover, it is envisaged by the present invention that the chemistry matrix includes one or more chemical reagents for reacting with the analyte to produce an electrochemical signal that represents the presence of the analyte in the sample fluid. In an embodiment, the one or more chemical reagents for reacting with the analyte to produce an electrochemical signal that represents the presence of the analyte in the sample fluid comprise a redox cofactor and/or an oxidoreductase as described herein above. In an embodiment, electrochemical properties include amperometric or coulometric responses indicative of the concentration of the analyte. See, for example, U.S. Pat. Nos. 5,108,564, 4,919,770 and 6,054,039.

In an embodiment, the electrochemical test element comprises at least two electrodes contacting the chemistry matrix comprised in said test element, or contacting means conductively connected to said test chemistry. In an embodiment, the means conductively connected to a chemistry matrix is a layer of a test strip connected to a chemistry matrix to enable diffusion of a redox cofactor and/or of a redox mediator through said layer. In a further embodiment, the means conductively connected to a chemistry matrix is a layer of a test strip at least partially overlaying and/or underlaying said chemistry matrix to enable diffusion of a redox cofactor and/or of a redox mediator through said layer.

The electrochemical property, according to the present invention, changes dependent on the activity of the oxidoreductase of the present invention. Thus, in an embodiment, the change of the electrochemical property only occurs if the oxidoreductase catalyzes the detection reaction. In a further embodiment, the change of electrochemical property is proportional to the number of catalytic cycles undergone by the oxidoreductase present in the chemistry matrix. Thus, in a further embodiment, the change of electrochemical property is proportional to the number of analyte molecules converted by the oxidoreductase.

In a further embodiment, the test element of the present invention is a combined optical and electrochemical test element. Accordingly, the test element, in an embodiment, has the structural features of an optical test element as well as the structural features of an electrochemical test element, i.e., in a further embodiment, at least two electrodes. Various formats have been described for combined test elements; e.g. US 2003/0068666 A1 describes a dual sensor with two reaction zones, making simultaneous electrochemical and colorimetric readings possible. Also, EP 1 318 397 A1 teaches a test strip with multiple reaction zones, and U.S. Pat. No. 8,460,539 B2 discloses a hybrid test strip with separate reaction zones for colorimetric and electrochemical detection.

Moreover, the present invention relates to a use of a tricyclic chemical compound according to the present invention or of a chemical compound as structurally defined the present specification, of a chemistry matrix according, or of a test element according to the present invention in an analytical or diagnostic test.

The term "test" is understood by the skilled person and relates to any process or method for assessing qualitatively or, in an embodiment, quantitatively the presence or absence of a compound of interest in a mixture of compounds.

In an embodiment, the analytical test is a test for assessing qualitatively or, in an embodiment, quantitatively the presence or absence of a redox cofactor as specified elsewhere herein, in a further embodiment of a reduced redox cofactor. Accordingly, the analytical test, in an embodiment, is a cell viability test, in a further embodiment, an in vitro cell viability test. However, also other embodiments including assessing the presence of reduced redox cofactors are envisaged, e.g. in testing for microbial contamination. In a further embodiment, the analytical test comprises detecting a reduced cofactor produced, e.g. by an oxidoreductase coupled to a molecule specifically binding to an antibody, in an embodiment, an anti-antibody immunoglobulin, in an immunological assay.

Accordingly, the present invention also relates to a use of a tricyclic chemical compound or a salt or solvate thereof according to the present invention or of a chemical compound comprising a heterocyclic group (Het) covalently bound to a π-acceptor group (Acc) according to the present invention for analyzing the viability or metabolism of cells.

In a further embodiment, the analytical or diagnostic test comprises qualitative and/or quantitative determination of any biological or chemical analyte detectable by optical or/and electrochemical means. In an embodiment, the analyte is comprised in a test sample of a subject, in a further embodiment a test sample of a body fluid. In a further embodiment, the analytical or diagnostic test comprises determining a glucose concentration in a test sample. In a further embodiment, the analytical or diagnostic test comprises determining a glucose concentration in a test sample from a subject suffering from diabetes or suspected to suffer from diabetes. Also in an embodiment, the analytical or diagnostic test is a test for monitoring blood glucose concentrations, in an embodiment, in a subject suffering from diabetes or suspected to suffer from diabetes. The analytical or diagnostic test, in an embodiment, is an in vitro test.

The term "analyte", as used herein, relates to a chemical compound present in a test sample of a subject, in an embodiment, in a body fluid. In an embodiment, the analyte is a small molecule, i.e., in an embodiment, the analyte is not a biological macromolecule. In a further embodiment, the analyte is an organic molecule, in a further embodiment, an organic molecule capable of undergoing a redox reaction in the presence of the test chemistry according to the present invention. In an embodiment, the analyte is a molecule of the subject's metabolism. Also in an embodiment, the analyte is a low molecular weight chemical compound, in a further embodiment, a chemical compound with a molecular mass of less than 1000 u (1000 Da; $1.66\times10^{-24}$ kg). In a further embodiment, the analyte is selected from the list consisting of malate, ethanol, ascorbic acid, cholesterol, glycerol, urea, 3-hydroxybutyrate, lactate, pyruvate, triglycerides, ketones, liver parameters, creatinine, HDL, and the like; in a further embodiment, the analyte is blood glucose.

As used herein, the term "subject" relates to a vertebrate. In an embodiment, the subject is a mammal, in a further embodiment, a mouse, rat, cat, dog, hamster, guinea pig, sheep, goat, pig, cattle, or horse. Still in a further embodiment, the subject is a primate. In a further embodiment, the subject is a human. In an embodiment, the subject is afflicted or suspected to be afflicted with a disease or condition associated with a measurable deviation from normal of at least one analyte. In a further embodiment, the subject is afflicted with diabetes.

As used herein, the term "body fluid" relates to all bodily fluids of a subject known to comprise or suspected to comprise the analyte of the present invention, including blood and blood products, plasma, serum, lacrimal fluid, urine, lymph, cerebrospinal fluid, bile, stool, sweat, interstitial fluid, and saliva. In an embodiment, the body fluid is plasma or serum. In a further embodiment, the body fluid is blood.

The term "test sample" is understood by the skilled person and relates to any suitably sized subportion of a tissue or, in an embodiment, of a body fluid of a subject. Body fluid test samples can be obtained by well known techniques including, e.g., venous or arterial puncture, epidermal puncture, and the like.

The term "diabetes" or "diabetes mellitus", as used herein, refers to disease conditions in which the glucose metabolism is impaired. Said impairment results in hyperglycemia. According to the World Health Organization (WHO), diabetes can be subdivided into four classes. Type 1 diabetes is caused by a lack of insulin. Insulin is produced by the so called pancreatic islet cells. Said cells may be destroyed by an autoimmune reaction in Type 1 diabetes (Type 1a). Moreover, Type 1 diabetes also encompasses an idiopathic variant (Type 1b). Type 2 diabetes is caused by an insulin resistance. Type 3 diabetes, according to the current classification, comprises all other specific types of diabetes mellitus. For example, the beta cells may have genetic defects affecting insulin production, insulin resistance may be caused genetically or the pancreas as such may be destroyed or impaired. Moreover, hormone deregulation or drugs may also cause Type 3 diabetes. Type 4 diabetes may occur during pregnancy. In an embodiment, diabetes as used herein refers to diabetes Type 1 or, in a further embodiment, Type 2. According to the German Society for Diabetes, diabetes is diagnosed either by a plasma glucose level being higher than 110 mg/dl in the fasting state or being higher than 220 mg/dl postprandial. Further diagnostic techniques for diagnosing diabetes, which may be used in conjunction with or in addition to the analytical or diagnostic tests of the present invention are well known in the art and are described in standard text books of medicine, such as Stedman or Pschyrembl.

It is understood by the skilled person that in diabetes, blood glucose levels have to be checked on a regular basis, in order to avoid and/or take countermeasures against hyperglycemia, e.g. after meals, or to avoid and/or take countermeasures against hypoglycemia, e.g. after administration of insulin. Accordingly, the present invention relates also to a chemical compound of the present invention for determining blood glucose levels, in a further embodiment, for use in diagnosing hyperglycemia, hypoglycemia, or normal glucose levels.

Moreover, the present invention relates to a use of a tricyclic chemical compound or a salt or solvate thereof according to the present invention or a chemical compound as structurally defined in the present specification for producing a chemistry matrix or for producing a test element.

Furthermore, the present invention relates to a method for determining the amount of an analyte in a test sample, comprising a) contacting said test sample with a tricyclic chemical compound according to the present invention or with a chemical compound as structurally defined in the present specification, with a chemistry matrix, or with a test element according to the present invention, b) estimating the amount of redox equivalents liberated or consumed by the chemical compound, by the chemical compound comprised in said chemistry matrix, or by the chemical compound comprised in said test element, in the presence of said test sample, and c) thereby determining the amount of an analyte in said test sample.

The method of the present invention, in an embodiment, is an in vitro method. Moreover, it may comprise steps in addition to those explicitly mentioned above. For example, further steps may relate, e.g., to obtaining a test sample for step a), or measuring at least one optical property of the chemical compound, the chemistry matrix, or the test element in the presence of said test sample in step b). Moreover, one or more of said steps may be performed by automated equipment. It is also understood by the skilled person that one or more steps of the method, e.g. the step of estimating the amount of redox equivalents liberated or consumed, may be repeated.

The term "determining" relates to measuring of the amount of an analyte in a sample, in an embodiment, semi-quantitatively or, in a further embodiment, quantitatively.

Methods of measuring the amount of redox equivalents, in an embodiment, electrons, liberated or consumed are known from the prior art. In an embodiment, the amount of redox equivalents liberated or consumed is measured by means of an optical or an electrochemical sensor. In a further embodiment, measuring the amount of redox equivalents liberated or consumed comprises detecting an optical property of a compound of the present invention as specified herein above.

In an embodiment, the method for determining the amount of an analyte in a test sample is a method for determining blood glucose levels in a subject, comprising
a) contacting said test sample with a tricyclic chemical compound according to the present invention or with a chemical compound as structurally defined in the present specification, with a chemistry matrix, or with a test element according to the present invention,
b) estimating the amount of redox equivalents liberated or consumed by the chemical compound, by the chemical compound comprised in said chemistry matrix, or by the chemical compound comprised in said test element, in the presence of said test sample, and
c) determining blood glucose levels in a subject based on the result of the estimation in step b).

It is understood by the skilled person that in case elevated levels of blood glucose are determined in a sample or, in an embodiment, in more than one sample from the same subject, the method of determining blood glucose levels may be a method assisting in diagnosing diabetes.

Also, the present invention relates to a method of maintaining blood glucose levels at appropriate levels in a subject, comprising the steps of the method for determining blood glucose levels in a subject as described above and the additional step of administering insulin to said subject in case an elevated level of blood glucose is determined, or administering glucose or a glucose-releasing compound (e.g. a starch-comprising food component) in case low levels of blood glucose are determined. As used herein, the term "elevated level of blood glucose" relates to blood glucose concentrations of more than 180 mg/dL, in an embodiment, more than 200 mg/dL; and the term "low levels of blood glucose" relates to blood glucose concentrations of less than 70 mg/dL, in an embodiment, less than 60 mg/dL.

Moreover, the present invention relates to a system for determining the amount of an analyte in a sample, comprising
a) a test element according to the present invention and
b) a device comprising a sensor for measuring the amount of redox equivalents liberated or consumed.

The term "device" is known to the skilled person and relates to technical equipment comprising at least one sensor for measuring the amount of redox equivalents liberated or consumed by a compound of the present invention. In an embodiment, said sensor is an optical and/or an electrochemical sensor; said sensors are known to the skilled person.

All references cited in this specification are herewith incorporated by reference with respect to their entire disclosure content and the disclosure content specifically mentioned in this specification.

Further optional features and embodiments of the invention will be disclosed in more detail in the subsequent description of examples. The respective optional features disclosed therein and in the definitions may be realized in an isolated fashion as well as in any arbitrary feasible combination, as the skilled person will realize. The scope of the invention is not restricted by the examples.

In the figures:

FIG. 1 Representative time-dependent UV/Vis spectra upon treating the indicator 1-methyl-3-[(E)-2-(1,3,3-trimethyl-3H-indolium-2-yl)ethenyl]quinolinium iodide trifluoromethanesulfonate (0.5 mM) with NADH (20 µM) in 50 mM phosphate buffer pH 7, showing a change in absorbance with λmax at 535 nm after adding NADH. The arrow indicates increasing time after addition of NADH; −NADH: no NADH added. x-axis: wavelength (λ, (nm)), y-axis: absorbance.

Figure 2:
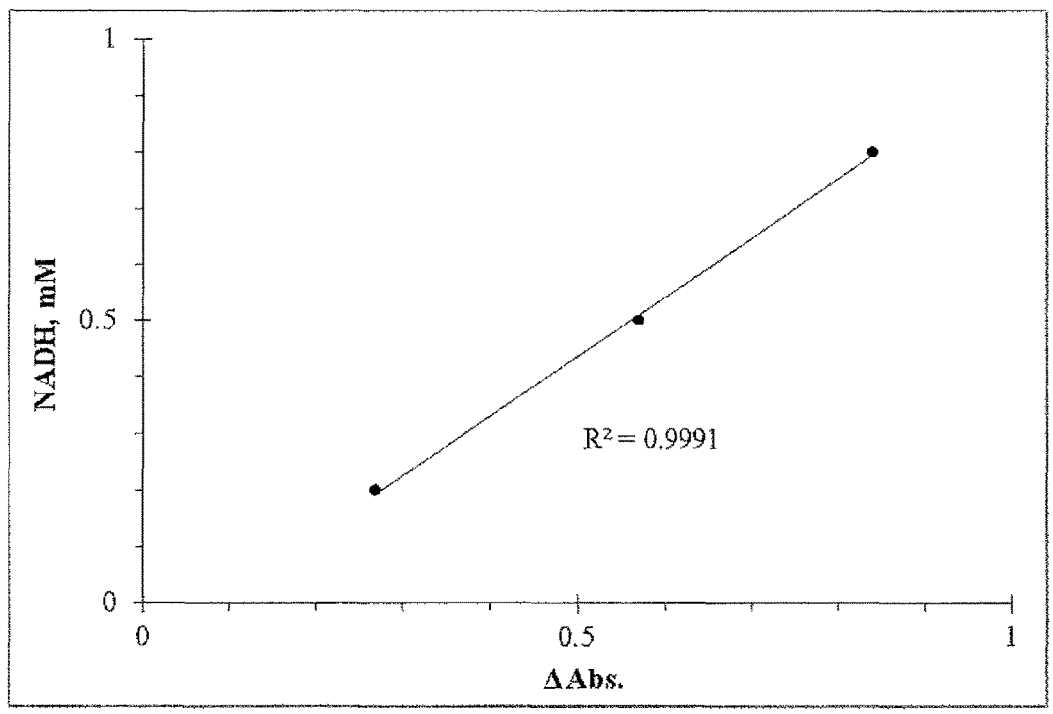

FIG. 2 Determination of NADH with the indicator 1-methyl-6-[(E)-2-(1,3,3-trimethyl-3H-indolium-2-yl)vinyl] quinolinium iodide trifluoromethanesulfonate. Absorbance change at 516 nm after 10 min vs. NADH concentration. x-axis: Absorption change at 516 nm, y-axis: NADH concentration (mM).

Figure 3:
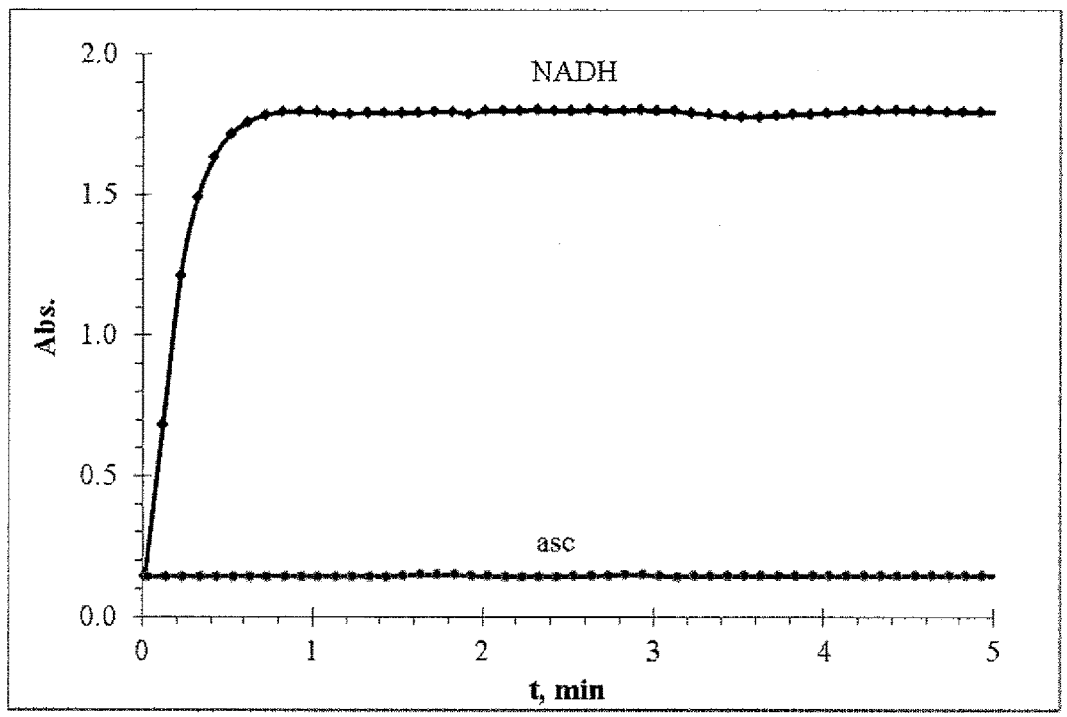

FIG. 3 Representative UV/Vis spectra of the kinetics upon treating of two solutions of the indicator 1-methyl-3-[(E)-2-(1,3,3-trimethyl-3H-indolium-2-yl)ethenyl]quinolinium iodide trifluoromethanesulfonate with NADH (disodium salt, 20 µM) or sodium ascorbate (asc, 20 µM) in phosphate buffer pH 7, respectively. x-axis: time (min), y-axis: absorbance.

Figure 4:
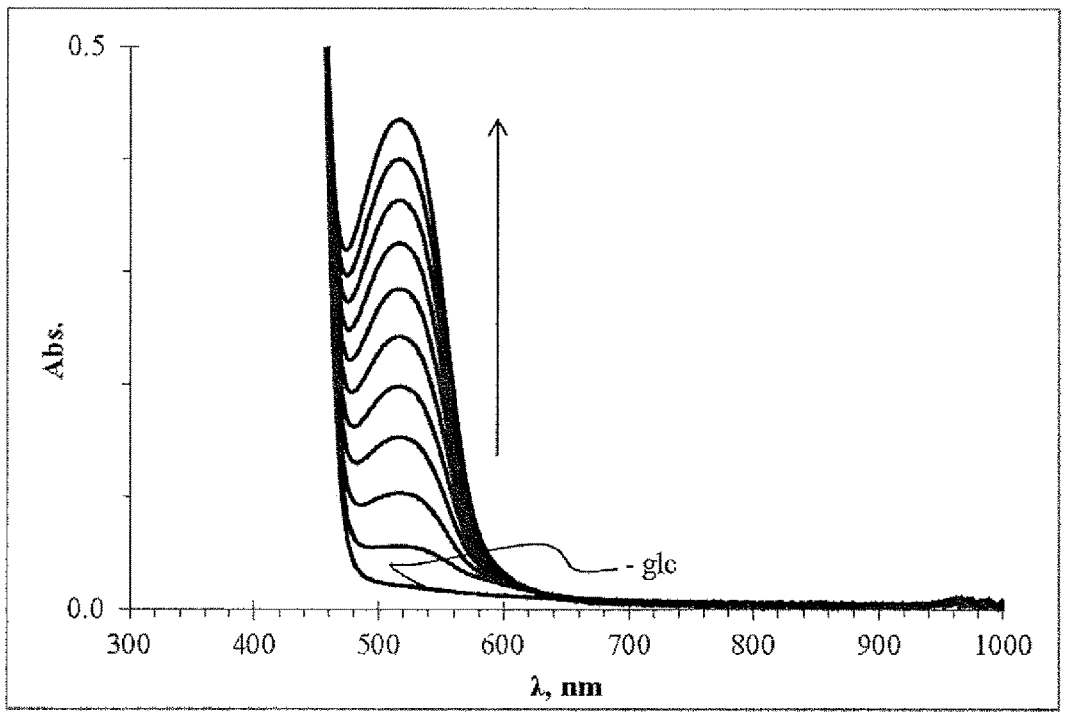

FIG. 4 Representative time-dependent UV/Vis spectra upon treating a mixture of 1-methyl-6-[(E)-2-(1,3,3-trimethyl-3H-indolium-2-yl)vinyl]quinolinium iodide trifluoromethanesulfonate (0.5 mM) and NAD/GlucDH2 with glucose (385 µM) in 100 mM phosphate buffer pH 7, showing a change in absorbance with λmax at 516 nm run after adding glucose. The arrow indicates increasing time after glucose addition; −glc: no glucose added. x-axis: wavelength (λ) (nm), y-axis: absorbance.

Figure 5:
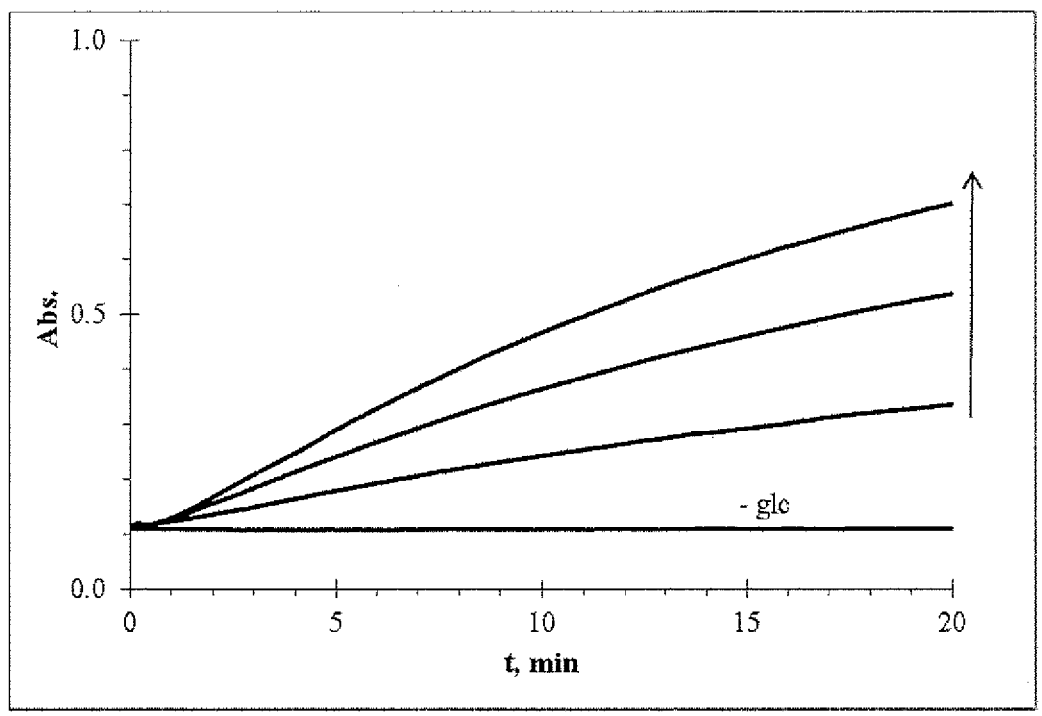

FIG. 5 Representative UV/Vis spectra of the kinetics upon treating the mixture of 1-methyl-6-[(E)-2-(1,3,3-trimethyl-3H-indolium-2-yl)vinyl]quinolinium iodide trifluoromethanesulfonate (0.5 mM) and NAD/GlucDH2 with glucose (0-385 µM) in 100 mM phosphate buffer pH 7. The arrow indicates increasing glucose concentrations (119 µM, 244 µM, and 385 µM, respectively); −glc: no glucose added. x-axis: time (min), y-axis: absorbance.

Figure 6:
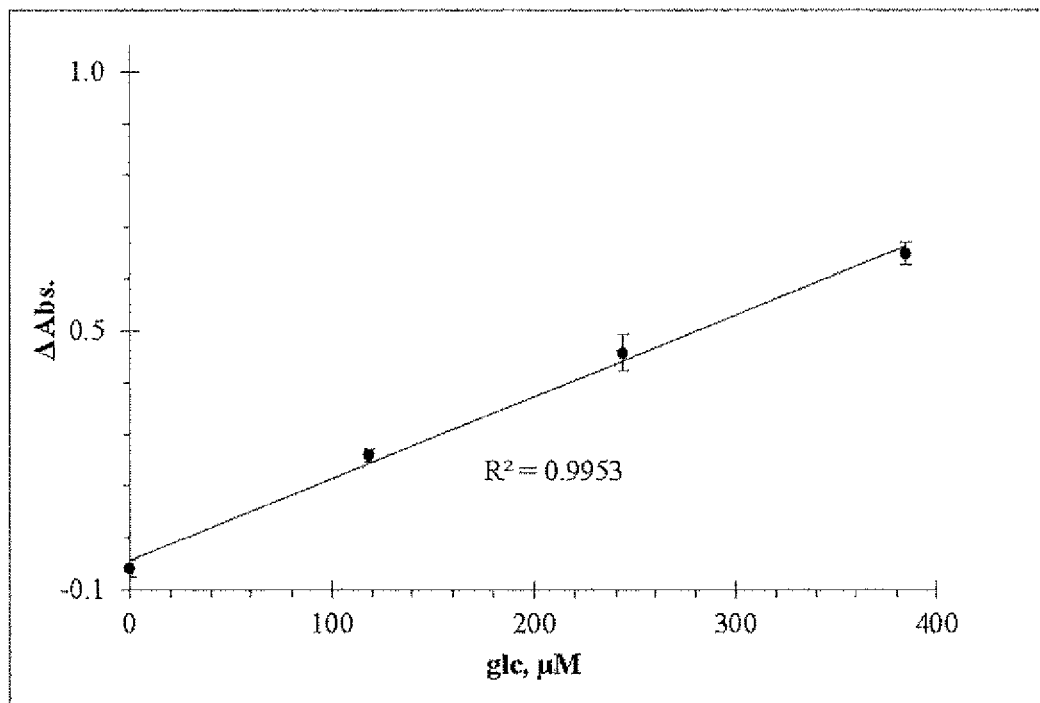

FIG. 6 Calibration plot corresponding to ΔAbs of the determination of glucose with the mixture of 1-methyl-6-[(E)-2-(1,3,3-trimethyl-3H-indolium-2-yl)vinyl]quinolinium iodide trifluoromethanesulfonate (0.5 mM) and NAD/GlucDH2 in 100 mM phosphate buffer pH 7 recorded at 517 nm after 20 min. Each point in the figure is a mean of three replicates, error bars represent the standard deviation. x-axis: glucose concentration (glc (µM)), y-axis: ΔAbs.

Figure 7:
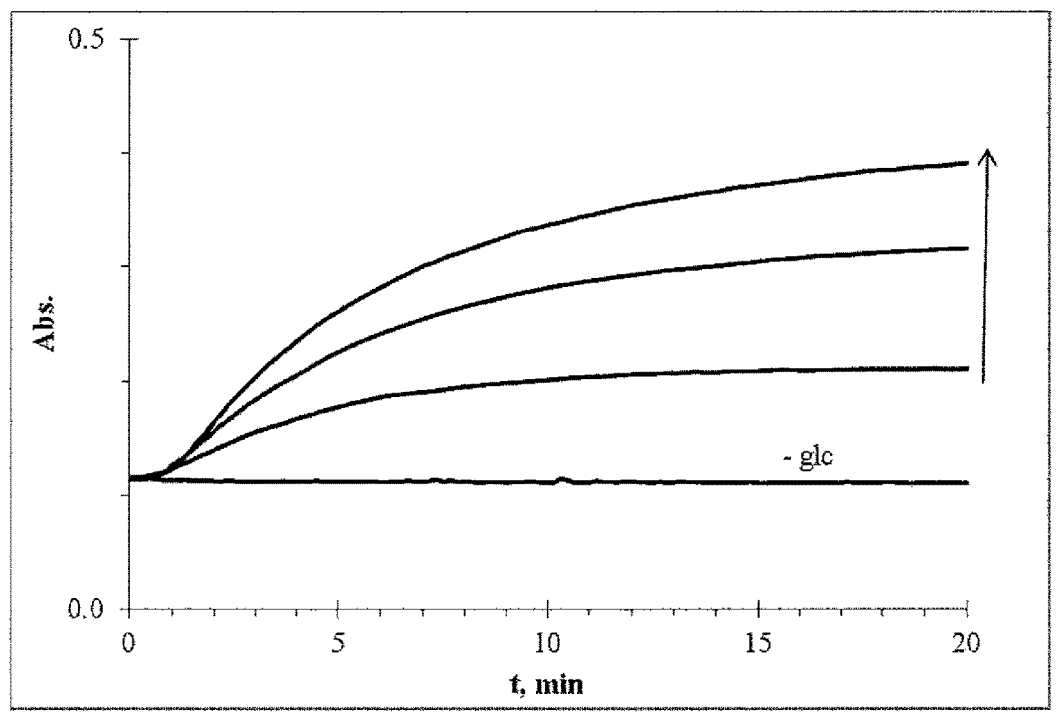

FIG. 7 Representative UV/Vis spectra of the kinetics upon treating the mixture of 1-methyl-6-[(E)-2-(1,3,3-trimethyl-3H-indolium-2-yl)vinyl]quinolinium iodide trifluoromethanesulfonate (0.5 mM) and carbaNAD/GlucDH2 with glucose (0-385 µM) in 100 mM phosphate buffer pH 7. The arrow indicates increasing glucose concentrations (119 µM, 244 µM, and 385 µM, respectively); −glc: no glucose added. x-axis: time (min), y-axis: absorbance.

Figure 8:
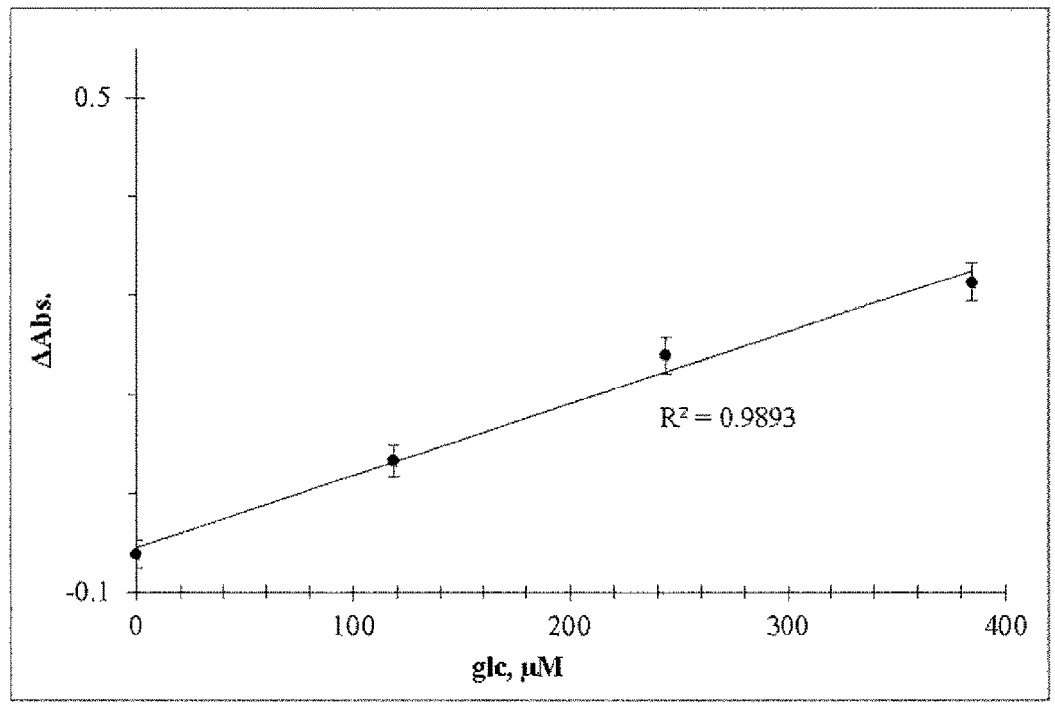

FIG. 8 Calibration plot corresponding ΔAbs of the determination of glucose with the mixture of 1-methyl-6-[(E)-2-(1,3,3-trimethyl-3H-indolium-2-yl)vinyl]quinolinium iodide trifluoromethanesulfonate (0.5 mM) and carbaNAD/GlucDH2 in 100 mM phosphate buffer pH 7 at 517 nm recorded after 20 min. Each point in the figure is a mean of three replicates, error bars represent the standard deviation. x-axis: glucose concentration (µM), y-axis: ΔAbs.

Figure 9:
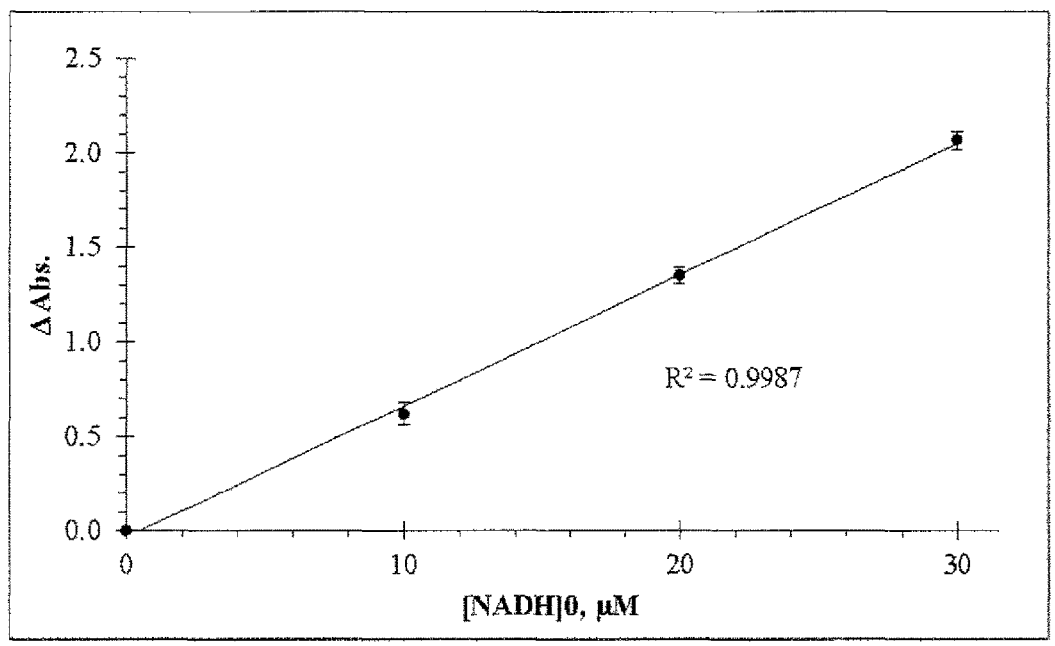

FIG. 9 Effects of the initial concentration of NADH on the change in absorbance of the reduced form of 1-methyl-3-[(E)-2-(1,3,3-trimethyl-3H-indolium-2-yl)ethenyl]quinolinium iodide trifluoromethanesulfonate recorded at 535 nm. Each point in the figure is a mean of three replicates; error bars represent the standard deviation. x-axis: initial NADH concentration ([NADH]$_0$ (µM)), y-axis: absorption change at 535 nm (ΔAbs).

Figure 10:
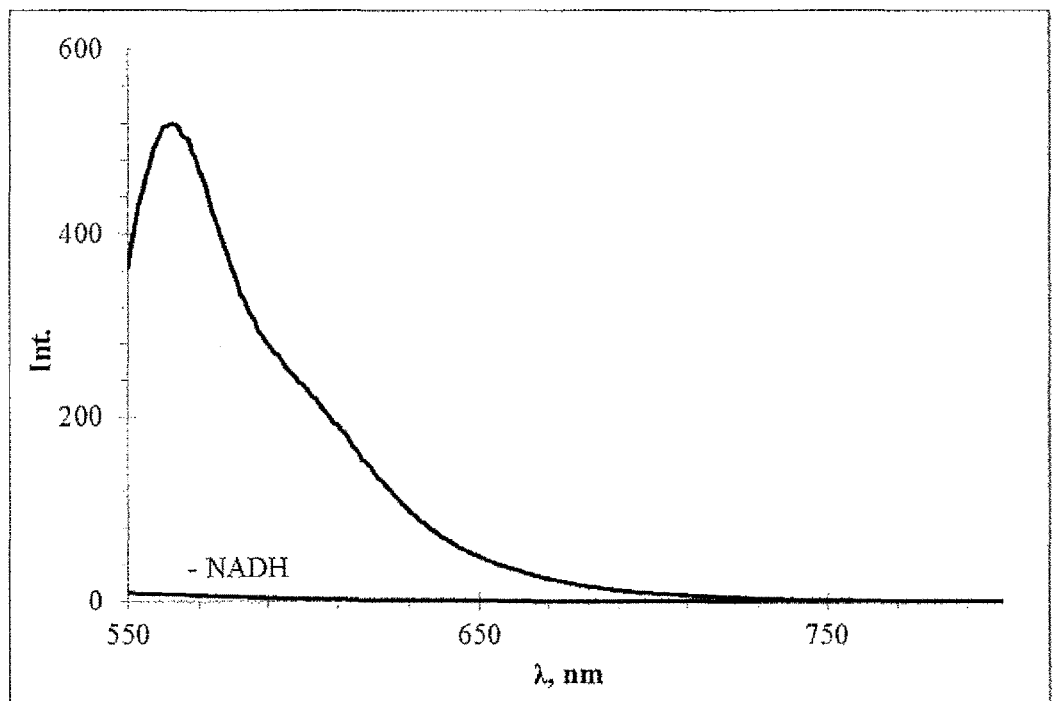

FIG. 10 Representative fluorescence emission spectra upon treating the indicator 1-methyl-3-[(E)-2-(1,3,3-trimethyl-3H-indolium-2-yl)ethenyl]quinolinium iodide trifluoromethanesulfonate (20 µM) with NADH (4 µM) in 10 mM PIPES pH 7, showing a change in fluorescence intensity with λmax at 560 nm after adding NADH using excitation at 535 nm; –NADH: no NADH added. x-axis: emission (λ (nm)), y-axis: fluorescence intensity.

Figure 11:
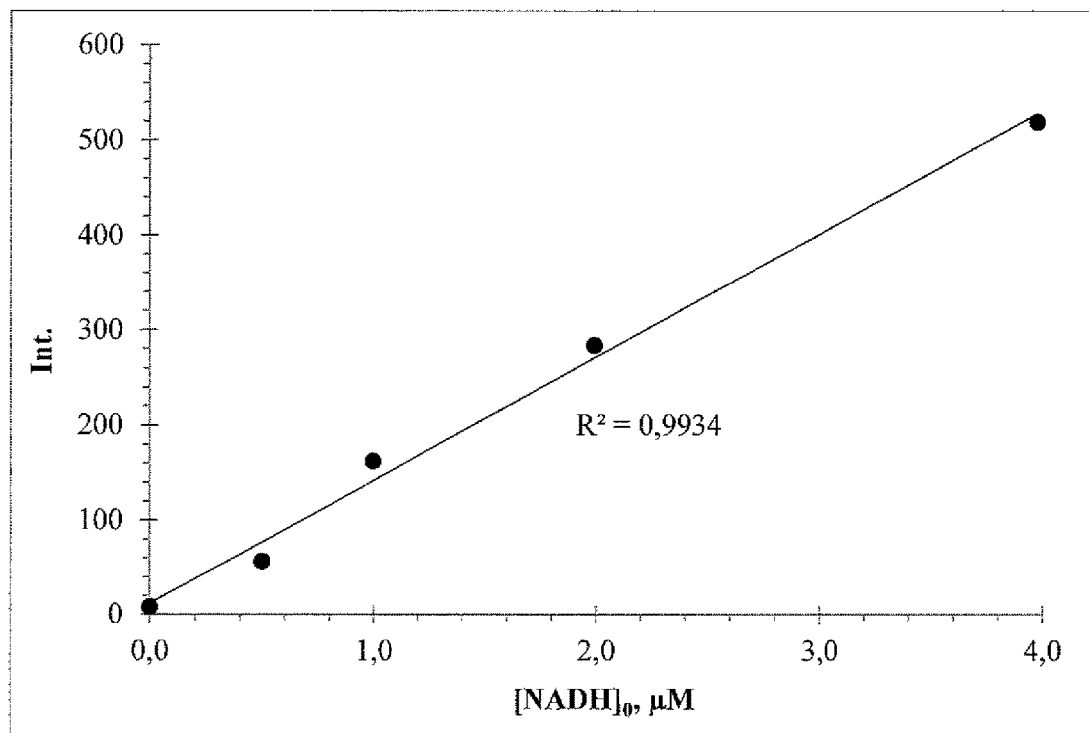

FIG. 11 Calibration plot correlating fluorescence changes of the indicator 1-methyl-3-[(E)-2-(1,3,3-trimethyl-3H-indolium-2-yl)ethenyl]quinolinium iodide trifluoromethanesulfonate (20 μM) with NADH concentration (0-4 μM). Measurements were performed in 10 mM PIPES pH 7 at 560 nm and were recorded after 30 min incubation, using excitation at 535 nm. x-axis: initial NADH concentration ($[NADH]_0$ (μM)), y-axis: fluorescence intensity.

EXAMPLES

Example 1

1-Methyl-6-((E)-3-oxo-3-phenyl-propenyl)-quinolinium methosulfate (MOPPQ)

1.1 Synthesis 1.1.1 Synthesis, Step 1: Synthesis of (E)-1-phenyl-3-quinolin-6-yl-propenone (XIV)

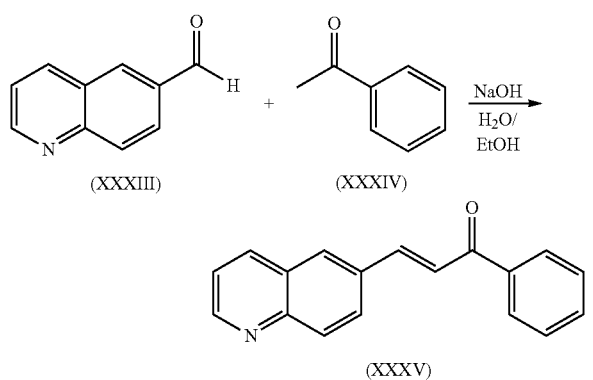

To a solution of 6-Quinolinecarbaldehyde (XXXIII) (500 mg, 3.18 mmol) in 50.0 ml EtOH and 6.40 ml NaOH (10% in $H_2O$) Acctophenone (XXXIV) (0.371 ml, 3.18 mmol) was added. The mixture was stirred at room temperature for 16 h and subsequently concentrated under reduced pressure. The remaining crude product was purified by silica gel chromatography (n-hexane/acetone; 75:25) obtaining 117.4 mg (14%) of the title compound.

1.1.2. Synthesis, Step 2: Synthesis of 1-methyl-6-((E)-3-oxo-3-phenyl-propenyl)-quinolinium methosulfate (MOPPQ, (XXII))

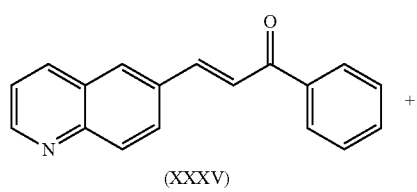

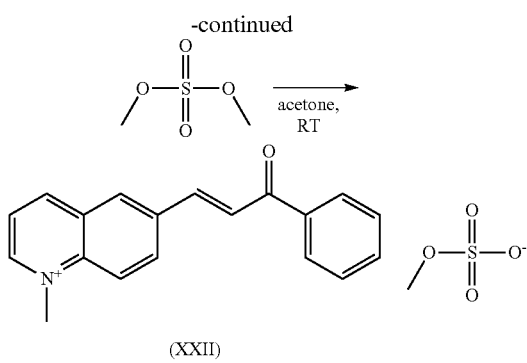

To a solution of (E)-1-phenyl-3-quinolin-6-yl-propenone (XXXV) (80.0 mg, 0.309 mmol) in 3.00 ml acetone dimethylsulfate (0.587 ml, 6.17 mmol) was added. The mixture was stirred 16 h at room temperature. The obtained suspension was filtered and the remaining precipitate was washed 3 times with acetone. The crude product was purified by preparative HPLC ($H_2O/CH_3CN$) obtaining 22.0 mg (18%) of the title compound (XXII).

1.2 Measurements 1.2.1 MOPPQ (XXII), Approximate Evaluation of the Reaction Rates with NADH and Ascorbate Two solutions of the redoxindicator 1-methyl-6-((E)-3-oxo-3-phenyl-propenyl)-quinolinium methosulfate (5.00 mg, 0.013 mmol) in 1.00 ml water were each treated with an excess of NADH (disodium salt) or sodium ascorbate, respectively. The solution treated with NADH changed rapidly from nearly colorless to orange. After a few minutes, a larger amount of an orange precipitate was obtained, probably the insoluble dihydrochinoline. In contrast, the solution treated with ascorbate showed only a pale orange color. Even after 16 h no precipitate was found. Thus, turnover rates of MOPPQ with NADH are much higher than with ascorbate.

Example 2

9-ethoxyphenazine-1-carbaldehyde 2.1 Synthesis, Step 1: Synthesis of (9-ethoxyphenazin-1-yl)methanol

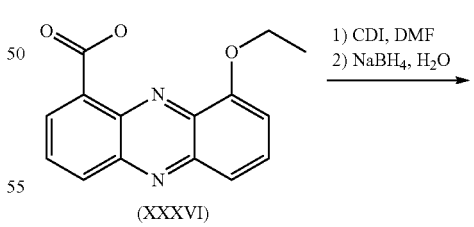

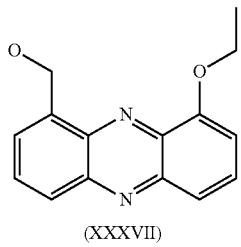

A suspension of 9-ethoxyphenazine-1-carboxylic acid (XXXVI) (1.50 g, 5.59 mmol) (synthesized from N-(2,6-difluorophenyl)-3-nitroanthranilic acid by a method in Rewcastle, G. W.; Denny, W. A. Synth. Commun. 1987, 17, 1171) in DMF (15 mL) was treated with 1,1'-carbonyldiimidazole (CDI) (1.85 g, 11.40 mmol), and the mixture was stirred at 50° C. for 1 h. After cooling, the mixture was diluted with DCM/petroleum ether (1:1) to complete precipitation of the imidazolide, which was collected, washed with petroleum ether, dried, dissolved in THF (200 mL) then slowly added to a solution of NaBH$_4$ in H$_2$O (50 mL). After stirring for 1 h, the mixture was neutralized by dropwise addition of concd HCl and then extracted with EtOAc. The organic layer was washed with aqueous Na$_2$CO$_3$, water, dried (Na$_2$SO$_4$), and evaporated, to give (9-ethoxyphenazin-1-yl)methanol (XXXVII) (1.20 g).

$^1$H NMR (CHLOROFORM-d, 400 MHz): δ [ppm]=8.16 (dd, J=8.8, 1.3 Hz, 1H), 7.81 (dd, J=8.8, 1.3 Hz, 1H), 7.79 (dd, J=8.8, 6.8 Hz, 1H), 7.76 (dd, J=8.8, 7.3 Hz, 1H), 7.68 (dd, J=6.8, 1.0 Hz, 1H), 7.06 (dd, J=7.3, 1.3 Hz, 1H), 5.36 (s, 2H), 5.26 (br. s., 1H), 4.34 (q, J=7.0 Hz, 2H), 1.66 (t, J=6.9 Hz, 3H)

$^{13}$C NMR (CHLOROFORM-d, 101 MHz): δ [ppm]= 154.4, 144.2, 143.7, 141.1, 139.1, 135.1, 131.0, 130.6, 128.8, 127.7, 120.9, 107.6, 64.8, 64.6, 14.7

LC-MS m/z 255.2 ([M+H]$^+$)

2.2 Synthesis, Step 2: Synthesis of 9-ethoxyphenazine-1-carbaldehyde

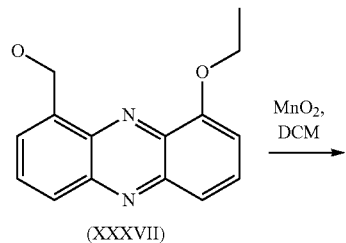

(XXXVII)

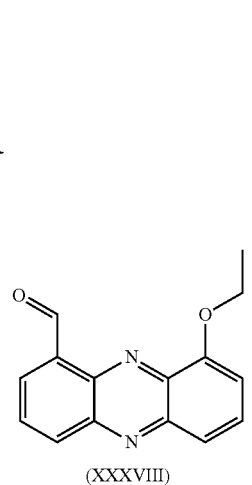

(XXXVIII)

A mixture of (9-ethoxyphenazin-1-yl)methanol (XXXVII) (750 mg, 2.95 mmol), activated manganese (IV) oxide (5.65 g, 58.5 mmol) and DCM (50 mL) was stirred at room temperature under an argon atmosphere for 3 h. After this time, the reaction was filtered through a pad of silica gel and concentrated. The residue was dissolved in EtOAc and the solution obtained was washed with aqueous Na$_2$CO$_3$, water, dried (Na$_2$SO$_4$), evaporated and dried under vacuum for 24 h to give 9-ethoxyphenazine-1-carbaldehyde (XXXVIII) (530 mg) as a yellow solid.

$^1$H NMR (CHLOROFORM-d, 400 MHz): δ [ppm]=11.63 (s, 1H), 8.52 (dd, J=8.7, 1.4 Hz, 1H), 8.48 (dd, J=7.1, 1.5 Hz, 1H), 7.99 (dd, J=8.3, 7.3 Hz, 1H), 7.78-7.87 (m, 2H), 7.14 (dd, J=6.8, 1.8 Hz, 1H), 4.39 (q, J=7.0 Hz, 2H), 1.70 (t, J=7.1 Hz, 3H)

$^{13}$C NMR (CHLOROFORM-d, 101 MHz): δ [ppm]= 191.3, 154.7, 144.4, 142.6, 141.1, 137.1, 135.7, 132.1, 131.6, 130.2, 130.0, 121.2, 108.4, 65.1, 14.7

LC-MS m/z 253.1 ([M+H]$^+$)

Example 3

Synthesis of 2-[(E)-2-(9-ethoxyphenazin-1-yl)vinyl]-1,3,3-trimethyl-3H-indolium iodide (XL)

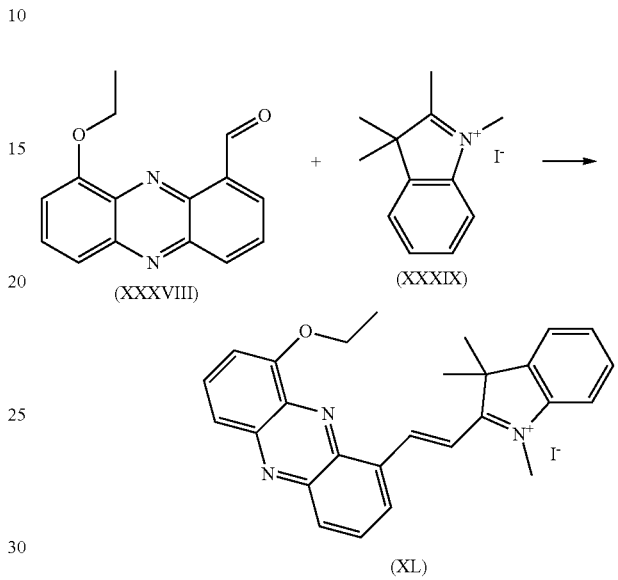

A mixture of 9-ethoxyphenazine-1-carbaldehyde (XXXVIII) (120 mg, 0.40 mmol) and 1,2,3,3-tetramethyl-3H-indolium iodide (XXXIX) (99 mg, 0.33 mmol) in ethanol (10 ml) was heated to reflux under an argon atmosphere for 3 h in the presence of piperidine (10 μL, 0.10 mmol). The reaction mixture was allowed to cool slowly to room temperature, and a red precipitate was filtered off, washed with cold ethanol, then with diethyl ether and dried. 120 mg, red powder was obtained.

$^1$H NMR (DMSO-d$_6$, 500 MHz): δ [ppm]=9.58 (d, J=16.7 Hz, 1H), 8.94 (d, J=6.9 Hz, 1H), 8.49 (d, J=8.5 Hz, 1H), 8.48 (d, J=16.7 Hz, 1H), 8.19 (dd, J=8.4, 7.4 Hz, 1H), 7.93-8.02 (m, 3H), 7.85 (d, J=8.5 Hz, 1H), 7.64-7.76 (m, 2H), 7.40 (d, J=7.6 Hz, 1H), 4.41 (q, J=6.8 Hz, 2H), 4.28 (s, 3H), 1.96 (s, 6H), 1.62 (t, J=6.9 Hz, 3H)

$^{13}$C NMR (DMSO-d$_6$, 101 MHz): δ [ppm]=182.0, 154.1, 147.3, 144.0, 143.7, 142.6, 141.9, 139.5, 135.5, 134.0, 132.5 (2C), 132.4, 131.1, 129.8, 129.2, 123.1, 120.4, 116.1, 115.6, 109.0, 64.5, 52.4, 34.9, 25.9 (2C), 14.8

LC-MS m/z 408.0 (M$^+$)

Example 4

Synthesis of (9E)-10,10-dimethyl-9-(quinolin-3-ylmethylene)-7,8,9,10-tetrahydro-6H-pyrido[1,2-a] indolium hexafluorophosphate (XLII)

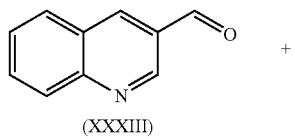

(XXXIII)

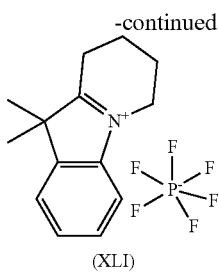

(XLI)

A mixture of quinoline-3-carbaldehyde (XXXIII) (500 mg, 3.18 mmol) and 10,10-dimethyl-7,8,9,10-tetrahydro-6H-pyrido[1,2-a]indolium hexafluorophosphate (XLI) (922 mg, 2.67 mmol) (synthesized from 2,3,3-trimethyl-3H-indole by a method in Mushkalo, I. L.; Turova, L. S.; Murovanaya, N. V. *Dopov. Akad. Nauk Ukr. RSR, Ser. B: Geol., Khim. Biol. Nauki* 1979, 1022) in ethanol (25 ml) was heated to reflux under an argon atmosphere for 16 h in the presence of piperidine (105 μL, 1.06 mmol). The reaction mixture was allowed to cool slowly to room temperature, and a precipitate was filtered off, washed with cold ethanol, then with diethyl ether and dried. 1.0 g, yellow powder was obtained.

$^1$H NMR (DMSO-$d_6$, 400 MHz): δ [ppm]=9.26 (d, J=2.0 Hz, 1H), 8.83 (s, 1H), 8.30 (s, 1H), 8.17 (d, J=7.8 Hz, 1H), 8.11 (d, J=8.3 Hz, 1H), 7.90-7.98 (m, 3H), 7.74 (t, J=7.5 Hz, 1H), 7.64-7.70 (m, 2H), 4.46 (t, J=5.6 Hz, 2H), 3.12 (t, J=5.2 Hz, 2H), 2.21 (t, J=5.6 Hz, 2H), 1.89 (s, 6H)

$^{13}$C NMR (DMSO-$d_6$, 101 MHz): δ [ppm]=181.03, 152.74, 147.89, 144.80, 144.54, 141.34, 139.27, 132.27, 130.51, 129.79, 129.47, 129.22, 128.33, 128.12, 127.99, 127.29, 123.39, 115.58, 53.16, 46.16, 26.15 (2C), 24.18, 19.73

LC-MS m/z 339.1 (M$^+$)

Example 5

Synthesis of Indolium Salts

The indolium salts listed in Table 1 are obtained analogously to example 3-4

TABLE 1

| Structure | LC-MS m/z, (M$^+$) | Remarks |
|---|---|---|
| (XLIII) | 263.1 | $^1$H NMR (DMSO-$d_6$, 400 MHz): δ [ppm] = 9.30 (d, J = 1.8 Hz, 1 H), 8.75 (dd, J = 4.8, 1.5 Hz, 1 H), 8.65 (dt, J = 8.1, 1.8 Hz, 1 H), 8.44 (d, J = 16.7 Hz, 1 H), 7.87-7.99 (m, 2 H), 7.82 (d, J = 16.7 Hz, 1 H), 7.65 (s, 3 H), 4.19 (s, 3 H), 1.81 (s, 6 H) $^{13}$C NMR (DMSO-$d_6$, 101 MHz): δ [ppm] = 181.8, 152.9, 151.6, 149.3, 143.8, 141.8, 136.1, 130.3, 129.8, 129.1, 124.2, 122.9, 115.6, 115.0, 52.5, 34.9, 25.0 (2C) |
| (XLIV) | 261.1 (M$^{2+}$) | $^1$H NMR (DMSO-$d_6$, 400 MHz): δ [ppm] = 9.10 (d, J = 2.3 Hz, 2 H), 8.60 (dd, J = 8.5, 2.4 Hz, 2 H), 8.39 (d, J = 16.4 Hz, 2 H), 7.87-7.99 (m, 6 H), 7.84 (d, J = 16.7 Hz, 2 H), 7.61-7.72 (m, 4 H), 4.19 (s, 6 H), 1.80 (s, 12 H) $^{13}$C NMR (DMSO-$d_6$, 101 MHz): δ [ppm] = 181.7, 152.4, 147.7, 145.1, 143.9, 141.8, 138.6, 130.1, 130.0, 129.1, 128.7, 122.9, 115.7 (4C), 52.5, 35.0, 24.9 (4C) |

TABLE 1-continued

| Structure | LC-MS m/z, (M⁺) | Remarks |
|---|---|---|
| (XLV) | 313.1 | $^1$H NMR (DMSO-d$_6$, 400 MHz): δ [ppm] = 9.66 (d, J = 2.0 Hz, 1 H), 9.23 (d, J = 1.8 Hz, 1 H), 8.62 (d, J = 16.4 Hz, 1 H), 8.08-8.15 (m, 2 H), 7.99 (d, J = 16.7 Hz, 1 H), 7.86-7.99 (m, 3 H), 7.76 (ddd, J = 8.0, 6.9, 1.0 Hz, 1 H), 7.63-7.70 (m, 2 H), 4.25 (s, 3 H), 1.86 (s, 6 H) $^{13}$C NMR (DMSO-d$_6$, 101 MHz): δ [ppm] = 181.7, 150.6, 149.5, 148.7, 143.8, 141.8, 138.5, 132.2, 129.8, 129.3, 129.1, 129.0, 127.9, 127.7, 127.1, 122.9, 115.5, 114.8, 52.4, 34.9, 25.1 (2C) |
| (XLVI) | 313.17 | $^1$H NMR (DMSO-d$_6$, 600 MHz): δ [ppm] = 9.04 (dd, J = 4.1, 1.7, 1 H), 8.83 (d, J = 1.8 Hz, 1 H), 8.63 (dd, J = 8.9, 2.0 Hz, 1 H), 8.62 (d, J = 16.4 Hz, 1 H), 8.48 (dd, J = 8.4, 1.2 Hz, 1 H), 8.17 (d, J = 8.9 Hz, 1 H), 7.90-7.98 (m, 2 H), 7.87 (d, J = 16.4 Hz, 1 H), 7.64-7.70 (m, 3 H), 4.23 (s, 3 H), 1.85 (s, 6 H) $^{13}$C NMR (DMSO-d$_6$, 151 MHz): δ [ppm] = 181.8, 152.9, 151.7, 149.3, 143.7, 141.8, 137.2, 133.7, 132.6, 129.9, 129.6, 129.0, 128.0, 127.8, 122.9, 122.7, 115.4, 114.4, 52.4, 34.8, 25.1 |
| (XLVIII) | 313.2 | $^1$H NMR (DMSO-d$_6$, 400 MHz): δ [ppm] = 9.53 (s, 1 H), 9.34 (s, 1 H), 8.94 (d, J = 16.4 Hz, 1 H), 8.44 (d, J = 8.3 Hz, 1 H), 8.31 (d, J = 8.1 Hz, 1 H), 7.97-8.09 (m, 2 H), 7.90 (d, J = 16.4 Hz, 1 H), 7.83-7.95 (m, 2 H), 7.64-7.73 (m, 2 H), 4.25 (s, 3 H), 1.88 (s, 6 H) $^{13}$C NMR (DMSO-d$_6$, 101 MHz): δ [ppm] = 182.0, 156.0, 146.3, 143.7, 143.5, 141.9, 132.9, 132.4, 129.9, 129.1, 128.8, 128.5, 127.7, 125.5, 123.0, 122.9, 116.9, 115.7, 52.7, 35.1, 25.2 (2C) |
| (XLIX) | 314.1 | $^1$H NMR (DMSO-d$_6$, 400 MHz): δ [ppm] = 9.41 (d, J = 16.7 Hz, 1 H), 9.18 (d, J = 1.8 Hz, 1 H), 9.14 (d, J = 1.8 Hz, 1 H), 8.91 (dd, J = 7.5, 0.9 Hz, 1 H), 8.39 (dd, J = 8.3, 1.0 Hz, 1 H), 8.16 (d, J = 16.9 Hz, 1 H), 8.12 (t, J = 8.1 Hz, 1 H), 7.95-8.01 (m, 1 H), 7.89-7.95 (m, 1 H), 7.65-7.71 (m, 2 H), 4.24 (s, 3 H), 1.87 (s, 6 H) $^{13}$C NMR (DMSO-d$_6$, 101 MHz): δ [ppm] = 181.9, 146.9, 146.3, 146.1, 143.6, 142.4, 141.9, 140.4, 134.0, 132.0, 130.5, 130.3, 129.8, 129.2, 122.9, 115.7, 115.6, 52.4, 34.9, 25.7 |

TABLE 1-continued

| Structure | LC-MS m/z, (M+) | Remarks |
|---|---|---|
| 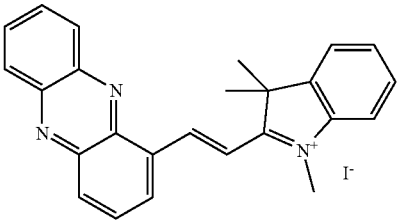 (L) | 364.18 | $^1$H NMR (DMSO-$d_6$, 600 MHz): δ [ppm] = 9.46 (d, J = 16.6 Hz, 1 H), 8.99 (d, J = 6.9 Hz, 1 H), 8.54 (dd, J = 8.7, 1.1 Hz, 1 H), 8.50 (d, J = 16.6 Hz, 1 H), 8.39-8.43 (m, 1 H), 8.33-8.37 (m, 1 H), 8.21 (dd, J = 8.7, 7.2 Hz, 1 H), 8.06-8.14 (m, 2 H), 8.00-8.04 (m, 1 H), 7.94-7.99 (m, 1 H), 7.68-7.73 (m, 2 H), 4.28 (s, 3 H), 1.95 (s, 6 H) $^{13}$C NMR (DMSO-$d_6$, 151 MHz): δ [ppm] = 182.0, 146.9, 143.6, 143.2, 142.8, 142.1, 141.9, 140.9, 134.2, 133.3, 132.3, 132.0 (2C), 130.8, 129.8, 129.7, 129.4, 129.1, 123.0, 116.3, 115.6, 52.4, 34.9, 25.7 (2C) |
| 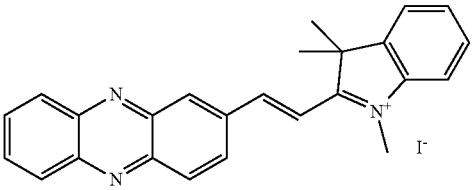 (LI) | 364.1806 | $^1$H NMR (DMSO-$d_6$, 500 MHz): δ [ppm] = 9.13 (d, J = 1.9 Hz, 1 H), 8.77 (dd, J = 9.5, 1.9 Hz, 1 H), 8.70 (d, J = 16.4 Hz, 1 H), 8.39 (d, J = 9.5 Hz, 1 H), 8.27- 8.33 (m, 2 H), 8.02-8.07 (m, 2 H), 7.99 (d, J = 16.4 Hz, 1 H), 7.95-7.99 (m, 1 H), 7.90-7.95 (m, 1 H), 7.62-7.73 (m, 2 H), 4.27 (s, 3 H), 1.88 (s, 6 H) $^{13}$C NMR (DMSO-$d_6$, 126 MHz): δ [ppm] = 181.7, 150.6, 144.3, 144.0, 143.6, 143.5, 142.7, 141.9, 136.7, 134.4, 132.4, 131.8, 130.2, 129.9, 129.6, 129.4, 129.1, 128.9, 123.0, 116.1, 115.6, 52.5, 35.0, 25.0 (2C) |

Example 6

Synthesis of 1-methyl-3-[(E)-2-(1,3,3-trimethyl-3H-indolium-2-yl)ethenyl]quinolinium iodide trifluoromethanesulfonate (XXIV)

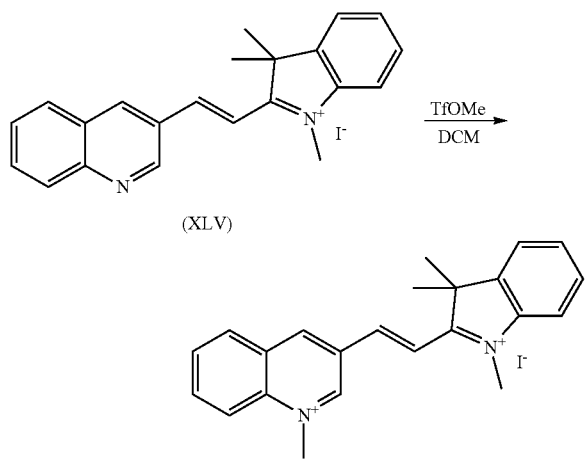

To a solution of 1,3,3-trimethyl-2-[(E)-2-(quinolin-3-yl)ethenyl]-3H-indolium iodide (XLV) (100 mg, 0.23 mmol) in 8 mL of dry DCM was added TfOMe (103 μL, 0.91 mmol) in dry DCM (2 mL) dropwise under an argon atmosphere. After the mixture was stirred for 16 h at room temperature, a precipitate was filtered off, washed with DCM (5×10 ml) and then with diethyl ether, and dried. 127 mg, yellow powder was obtained.

$^1$H NMR (DMSO-$d_6$, 400 MHz): δ [ppm]=10.16 (s, 1H), 9.93 (s, 1H), 8.61 (d, J=8.6 Hz, 1H), 8.59 (d, J=16.7 Hz, 1H), 8.50 (d, J=7.8 Hz, 1H), 8.37-8.44 (m, 1H), 8.17 (t, J=7.6 Hz, 1H), 8.05 (d, J=16.7 Hz, 1H), 8.00-8.03 (m, 1H), 7.92-7.97 (m, 1H), 7.68-7.76 (m, 2H), 4.70 (s, 3H), 4.26 (s, 3H), 1.85 (s, 6H)
$^{13}$C NMR (DMSO-$d_6$, 101 MHz): δ [ppm]=181.3, 150.9, 146.4, 144.8, 144.1, 141.9, 138.5, 137.2, 131.4, 131.1, 130.4, 129.3, 128.7, 128.3, 123.1, 122.3 (TfO$^-$), 119.7, 119.1 (TfO$^-$), 117.4, 116.0, 52.7, 46.1, 35.3, 24.7 (2C)
LC-MS m/z 327.2 ([M–H]$^+$), 345.1 ([M+HO$^-$]$^+$)
UV-Vis (50 mM phosphate buffer pH=7): max 512 (weak), 384, 311 nm; after reduction with NADH: 535, 528sh nm;
Solubility in water: ≥10 mM Example 7

Synthesis of Diquaternary Salts

The diquaternary salts listed in Table 2 are obtained by reacting indolium salts (from examples 3-5) with various triflate alkylating agents analogously to example 6. The temperature and time of reaction can usually be varied over wide ranges. The product is crystallized from a suitable solvent and, if required, the anion can be changed by conventional procedures, for example by the use of ion exchange resins.

TABLE 2

| Structure | Remarks |
|---|---|
| (XXIII) | $^{1}$H NMR (DMSO-d$_6$, 400 MHz): δ [ppm] = 9.63 (s, 1 H), 9.26 (d, J = 8.3 Hz, 1 H), 9.09 (d, J = 6.1 Hz, 1 H), 8.41 (d, J = 16.7 Hz, 1 H), 8.32 (dd, J = 8.1, 6.3 Hz, 1 H), 8.01 (s, 1 H), 7.97 (d, J = 16.9 Hz, 1 H), 7.90-7.94 (m, 1 H), 7.67-7.75 (m, 2 H), 4.42 (s, 3 H), 4.23 (s, 3 H), 1.81 (s, 6 H)<br>$^{13}$C NMR (DMSO-d$_6$, 101 MHz): δ [ppm] = 181.3, 146.9, 146.7, 144.1, 143.7, 143.4, 141.8, 133.9, 130.5, 129.3, 127.8, 123.0, 122.3 (TfO$^-$), 119.1 (TfO$^-$), 118.6, 116.1, 52.8, 48.4, 35.4, 24.5 (2C)<br>LC-MS m/z 277.1 ([M − H]$^+$), 295.2 ([M + HO$^-$]$^+$)<br>UV-Vis (50 mM phosphate buffer pH = 7): λmax 364, 290, 251 nm; after reduction with NADH: 546, 530sh. nm; Solubility in water: ≥ 114 mM |
| (XXIV) | $^{1}$H NMR (DMSO-d$_6$, 400 MHz): δ [ppm] = 8.78 (d, J = 2.5 Hz, 2 H), 8.39 (dd, J = 9.6, 2.5 Hz, 2 H), 8.25 (d, J = 15.9 Hz, 2 H), 7.76-7.87 (m, 4 H), 7.58 (quind, J = 7.4, 1.1 Hz, 4 H), 7.31 (d, J = 16.2 Hz, 2 H), 6.63 (d, J = 9.6 Hz, 2 H), 4.04 (s, 6 H), 3.54 (s, 6 H), 1.74 (s, 12 H)<br>$^{13}$C NMR (DMSO-d$_6$, 101 MHz): δ [ppm] = 181.1, 161.6, 150.0, 149.2, 143.1, 141.9, 136.6, 128.9, 128.8, 122.8, 122.3 (TfO$^-$), 119.7, 119.1 (TfO$^-$), 114.7, 114.6, 108.5, 51.6, 37.6, 33.9, 25.6 (4C)<br>UV-Vis (water): λmax 369, 310sh, 218 nm; after reduction with NADH: 650, 538 nm; Solubility in water: ≥ 15 mM |
| (XXVI) | $^{1}$H NMR (DMSO-d$_6$, 400 MHz): δ [ppm] = 10.17 (s, 1 H), 9.94 (s, 1 H), 8.71 (d, J = 8.8 Hz, 1 H), 8.59 (d, J = 16.7 Hz, 1 H), 8.51 (d, J = 8.1 Hz, 1 H), 8.39 (t, J = 8.0 Hz, 1 H), 8.16 (t, J = 7.5 Hz, 1 H), 8.06 (d, J = 16.7 Hz, 1 H), 8.02 (s, 1 H), 7.92- 7.97 (m, 1 H), 7.70-7.75 (m, 2 H), 5.14 (q, J = 7.1 Hz, 2 H), 4.27 (s, 3 H), 1.86 (s, 6 H), 1.72 (t, J = 7.2 Hz, 3 H)<br>$^{13}$C NMR (DMSO-d$_6$, 101 MHz): δ [ppm] = 181.3, 150.2, 146.3, 144.9, 144.0, 141.8, 137.5, 137.4, 131.8, 130.9, 130.4, 129.3, 129.2, 128.5, 123.0, 122.3 (TfO$^-$), 119.3, 119.1 (TfO$^-$), 117.4, 116.0, 53.9, 52.7, 35.3, 24.7 (2C), 15.0<br>LC-MS m/z 341.2 ([M − H]$^+$), 359.1 ([M + HO$^-$]$^+$)<br>UV-Vis (50 mM phosphate buffer pH = 7): λmax 512 (weak), 384, 311, 241 nm; after reduction with NADH: 535, 528sh nm; Solubility in water: ≥ 4 mM |

TABLE 2-continued

| Structure | Remarks |
|---|---|
| 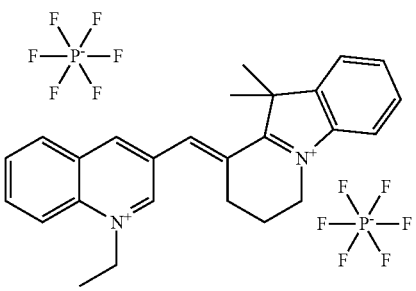<br>(XXVII) | $^1$H NMR (DMSO-$d_6$, 400 MHz): δ [ppm] = 9.91 (s, 1 H), 9.54 (s, 1 H), 8.68 (d, J = 8.8 Hz, 1 H), 8.61 (d, J = 8.1 Hz, 1 H), 8.37 (t, J = 7.8 Hz, 1 H), 8.23 (s, 1 H), 8.14 (t, J = 7.8 Hz, 1 H), 8.00 (d, J = 7.6 Hz, 1 H), 7.95 (d, J = 7.1 Hz, 1 H), 7.72 (quin, J = 6.7 Hz, 2 H), 5.15 (q, J = 7.1 Hz, 2 H), 4.52 (t, J = 5.3 Hz, 2 H), 3.07-3.20 (m, J = 5.1, 5.1 Hz, 2 H), 2.18-2.30 (m, J = 4.8, 4.8 Hz, 2 H), 1.90 (s, 6 H), 1.69 (t, J = 7.1 Hz, 3 H)<br>$^{13}$C NMR (DMSO-$d_6$, 101 MHz): δ [ppm] = 180.1, 151.7, 147.2, 147.2, 144.3, 141.0, 139.7, 137.0, 136.5, 131.8, 130.6, 130.6, 130.2, 129.2, 129.2, 128.1, 123.0, 119.0, 115.6, 53.6, 53.0, 46.2, 25.4 (2C), 23.1, 19.2, 15.2<br>LC-MS m/z 367.1 ([M − H]$^+$), 385.1 ([M + HO$^−$]$^+$)<br>UV-Vis (50 mM phosphate buffer pH = 7): λmax 361, 237, 212 nm; after reduction with NADH: 550, 530sh nm (Cl$^−$ form);<br>Solubility in water: ≥ 0.3 mM (Cl$^−$ form) |
| 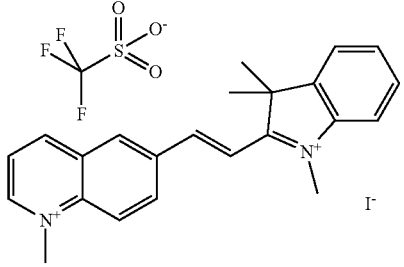<br>(XVIII) | $^1$H NMR (DMSO-$d_6$, 600 MHz): δ [ppm] = 9.56 (d, J = 5.7 Hz, 1 H), 9.26 (d, J = 8.4 Hz, 1 H), 9.16 (s, 1 H), 9.04 (dd, J = 9.4, 1.9 Hz, 1 H), 8.68 (d, J = 9.3 Hz, 1 H), 8.64 (d, J = 16.5 Hz, 1 H), 8.26 (dd, J = 8.4, 5.7 Hz, 1 H), 8.01 (d, J = 16.6 Hz, 1 H), 7.96-8.01 (m, 1 H), 7.92-7.96 (m, 1 H), 7.67-7.73 (m, 2 H), 4.69 (s, 3 H), 4.26 (s, 3 H), 1.85 (s, 6 H) (Cl$^−$ form)<br>$^{13}$C NMR (METHANOL-$d_4$, 151 MHz): δ [ppm] = 184.2, 152.6, 150.7, 150.8, 149.7, 145.5, 143.4, 141.9, 137.4, 135.8, 134.5, 132.0, 130.9, 124.3, 124.2, 121.3, 118.4, 116.9, 54.7, 46.7, 36.0, 25.9 (2C) (Cl$^−$ form)<br>LC-MS m/z 164.10 (M$^{2+}$)<br>UV-Vis (50 mM phosphate buffer pH = 7): λmax 377, 317 nm; after reduction with NADH: 517 nm;<br>Solubility in water: ≥ 15 mM |
| 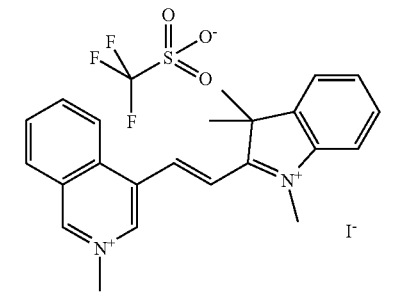<br>(XXX) | $^1$H NMR (DMSO-$d_6$, 400 MHz): δ [ppm] = 10.10 (s, 1 H), 9.35 (s, 1 H), 8.86 (d, J = 16.4 Hz, 1 H), 8.67 (d, J = 8.6 Hz, 1 H), 8.60 (d, J = 8.3 Hz, 1 H), 8.42 (t, J = 7.6 Hz, 1 H), 8.19 t, J = 7.6 Hz, 1 H), 8.02-8.08 (m, 1 H), 7.95-8.00 (m, 1 H), 7.89 (d, J = 16.2 Hz, 1 H), 7.69-7.77 (m, 2 H), 4.56 (s, 3 H), 4.28 (s, 3 H), 1.88 (s, 6 H)<br>LC-MS m/z 327.2 ([M − H]$^+$), 345.1 ([M + HO$^−$]$^+$)<br>UV-Vis (water): λmax 371 nm; after reduction with NADH: 520sh, 492 nm;<br>Solubility in water: ≥ 25 mM |
| 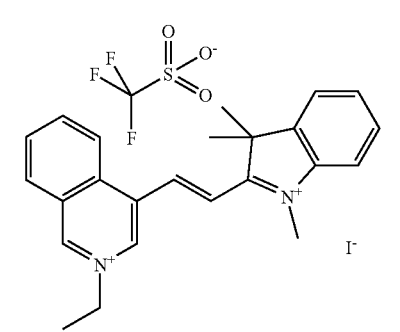<br>(XXXI) | $^1$H NMR (DMSO-$d_6$, 400 MHz): δ [ppm] = 10.19 (s, 1 H), 9.41 (s, 1 H), 8.85 (d, J = 16.4 Hz, 1 H), 8.67 (d, J = 8.6 Hz, 1 H), 8.60 (d, J = 8.3 Hz, 1 H), 8.43 (t, J = 7.7 Hz, 1 H), 8.20 (t, J = 7.6 Hz, 1 H), 8.03-8.09 (m, 1 H), 7.95-7.99 (m, 1 H), 7.91 (d, J = 16.4 Hz, 1 H), 7.70-7.79 (m, 2 H), 4.83 (q, J = 7.2 Hz, 2 H), 4.29 (s, 3 H), 1.88 (s, 6 H), 1.75 (t, J = 7.3 Hz, 3 H)<br>LC-MS m/z 341.2 ([M − H]$^+$), 359.1 ([M + HO$^−$]$^+$) |

TABLE 2-continued

| Structure | Remarks |
|---|---|
| (XXXII) | ¹H NMR (METHANOL-d₄, 400 MHz): δ [ppm] = 9.76 (d, J = 3.0 Hz, 1 H), 9.57 (d, J = 2.3 Hz, 1 H), 9.51 (d, J = 16.7 Hz, 1 H), 9.12 (d, J = 7.6 Hz, 1 H), 8.82 (d, J = 8.8 Hz, 1 H), 8.52 (dd, J = 8.7, 7.7 Hz, 1 H), 8.17 (d, J = 16.9 Hz, 1 H), 7.95 (s, 1 H), 7.86 (s, 1 H), 7.69-7.77 (m, 2 H), 4.88 (s, 3 H), 4.34 (s, 3 H), 1.95 (s, 6 H) UV-Vis (water): λmax 408, 347, 247 nm; after reduction with NADH: 535sh nm; Solubility in water: ≥ 9 mM |
| (XX) | ¹H NMR (MeOD, 400 MHz): δ [ppm] = 9.70 (d, J = 16.7 Hz, 1 H), 9.13 (d, J = 6.3 Hz, 1 H), 9.05 (d, J = 8.8 Hz, 1 H), 8.90 (d, J = 9.1 Hz, 1 H), 8.79-8.87 (m, 1 H), 8.56-8.74 (m, 2 H), 8.38-8.45 (m, 1 H), 8.29 (d, J = 16.4 Hz, 1 H), 7.93-8.00 (m, 1 H), 7.85-7.92 (m, 1 H), 7.67-7.80 (m, 2 H), 5.15 (br. s., 3 H), 4.38 (s, 3 H), 2.03 (s, 6 H) LC-MS m/z 189.60 (M²⁺) UV-Vis (50 mM phosphate buffer pH = 7): λmax 481, 394, 377sh., 261 nm; after reduction with NADH: 806sh., 740 nm; Solubility in water: ≥ 4 mM |
| (XXI) | LC-MS m/z 423.1 (M⁺) HRMS m/z 422.2237 ([M − H]⁺) UV-Vis (50 mM phosphate buffer pH = 7): λmax 516sh., 442, 390, 278 nm; after reduction with NADH: 746 nm; Solubility in water: ≥ 7 mM |
| (LII) | LC-MS m/z 379.3 (M⁺) HRMS m/z 378.1970 ([M − H]⁺) UV-Vis (water) after reduction with NADH: λmax 740 nm; |

Example 8

Reaction of an Indicator with NADH

The following were mixed in a cuvette: 50 µL of 10 mM solution of an indicator (1-methyl-3-[(E)-2-(1,3,3-trimethyl-3H-indolium-2-yl)ethenyl]quinolinium iodide trifluoromethanesulfonate) in distilled water, 950 µL of 50 mM phosphate buffer pH 7, 2 µL of 10 mM NADH solution in distilled water. A UV/Vis spectrum (400-1000 nm) was recorded every 7.5 sec for a 1 min after addition of NADH (resolution 2 nm) (FIG. 1). No further color change could be measured after 52.5 sec.

UV/Vis spectral properties of further indicators according to the invention listed in Table 3.

TABLE 3
Redoxindicators. UV/Vis studies
| Indicator | UV/Vis oxidized form (nm) 50 mM phosphate buffer pH = 7 | UV/Vis reduced form (nm) 50 mM phosphate buffer pH = 7 |
|---|---|---|
| 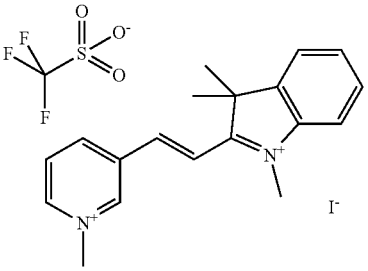<br>(XXIII) | 364, 290, 251 | 546, 530sh. |
| 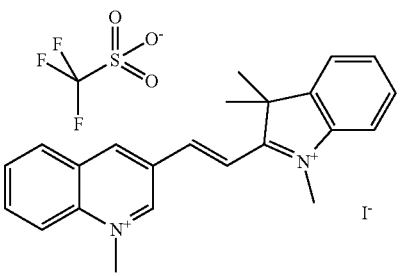<br>(XXV) | 512 (weak), 384, 311 | 535, 528sh |
| 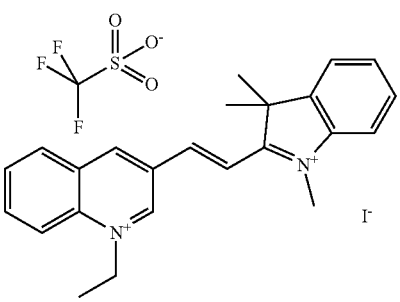<br>(XXVI) | 384, 311, 241 | 535, 528sh |
| 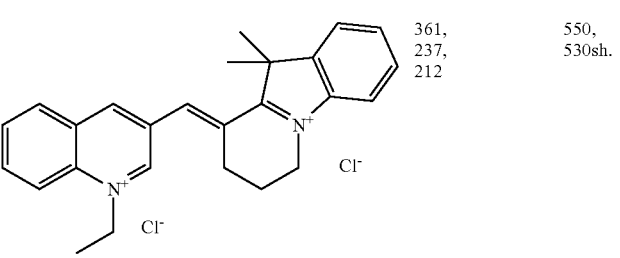<br>(XXVII) | 361, 237, 212 | 550, 530sh. |

TABLE 3-continued

Redoxindicators. UV/Vis studies

| Indicator | UV/Vis oxidized form (nm) 50 mM phosphate buffer pH = 7 | UV/Vis reduced form (nm) 50 mM phosphate buffer pH = 7 |
|---|---|---|
| (XVIII) | 377, 317 | 517 |
| (XX) | 481, 394, 377sh., 261 | 806sh., 740 |
| (XXI) | 516sh., 442, 390, 278 | 746 |

Example 9

Determination of NADH

The following were mixed in a cuvette: 100 μL of 10 mM solution of an indicator (1-methyl-6-[(E)-2-(1,3,3-trimethyl-3H-indolium-2-yl)vinyl]quinolinium iodide trifluoromethanesulfonate) in distilled water, 1000 μL of 50 mM phosphate buffer pH 7, 20-80 μL of 10 mM NADH solution in distilled water. Change in absorbance at 516 nm was recorded after 10 min (FIG. 2).

Example 10

1-Methyl-3-[(E)-2-(1,3,3-trimethyl-3H-indolium-2-yl)ethenyl]quinolinium iodide trifluoromethanesulfonate, Evaluation of the Reaction Rates with NADH and Ascorbate Two solutions of the redoxindicators 1-methyl-3-[(E)-2-(1,3,3-trimethyl-3H-indolium-2-yl)ethenyl]quinolinium iodide trifluoromethanesulfonate (0.005 mmol) in 1.00 ml of 50 mM phosphate buffer pH 7 were each treated with 2 μL of 10 mM NADH (disodium salt) or sodium ascorbate solutions in distilled water, respectively. The absorbance at 535 nm was measured in relation to time (FIG. 3). The solution treated with NADH changed rapidly from nearly colorless to pink. In contrast, the solution treated with ascorbate did not change color. Thus, turnover rates of 1-methyl-3-[(E)-2-(1,3,3-trimethyl-3H-indolium-2-yl)ethenyl]quinolinium iodide trifluoromethanesultrifluoromethanesulfonate with NADH are much higher than with ascorbate.

Example 11

Determination of Glucose with GlucDH2/an Indicator 11.1 Measurement 1: Change in Absorbance Upon Reaction with Glucose and GlucDH2/NAD The following were mixed in a cuvette: 500 μL of 1.0 mM solution of an indicator (1-methyl-6-[(E)-2-(1,3,3-trimethyl-3H-indolium-2-yl)vinyl]quinolinium iodide trifluoromethanesulfonate) in 100 mM phosphate buffer pH 7, 500 μL of glucose dehydrogenase 2 (GlucDH2) solution (in 100 mM phosphate buffer pH 7 containing 4.0 mM NAD$^+$) at a concentration of 491 U/ml, 40 μL of 10 mM solution of glucose in distilled water. A UV/Vis spectrum (300-1000 nm) was recorded every 1 min for a 10 min after addition of glucose (resolution 1 nm) (FIG. 4).

11.2 Measurement 2: Kinetics of Reaction with Glucose and GlucDH2/NAD

The reaction mixture was the same as in Measurement 1, except for 10-40 μL samples of 10 mM solution of glucose in distilled water were used. The absorbance at 517 nm was recorded every 10 sec for a 20 min after addition of glucose (FIG. 5, 6).

11.3 Measurement 3: Kinetics of Reaction with Glucose and GlucDH2/carbaNAD

Conditions were the same as in Measurement 2, with carbaNAD replacing NAD. The absorbance at 517 nm was recorded every 10 sec for a 20 min after addition of glucose (FIG. 7, 8).

Example 12

1-Methyl-3-[(E)-2-(1,3,3-trimethyl-3H-indolium-2-yl)ethenyl]quinolinium iodide trifluoromethanesulfonate, Evaluation of Extinction Coefficient (ε) Under Pseudo-First-Order Reaction Conditions The following were mixed in a cuvette: 100 μL of 10 mM solution of 1-methyl-3-[(E)-2-(1,3,3-trimethyl-3H-indolium-2-yl)ethenyl]quinolinium iodide trifluoromethanesulfonate in distilled water, 900 μL of 50 mM phosphate buffer pH 7, 1-3 μL of 10 mM NADH in distilled water. Change in absorbance at 535 nm was recorded after 5 min, when no further color change could be measured (FIG. 3, 9).

FIG. 9 shows that concentration of the reduced form of 1-methyl-3-[(E)-2-(1,3,3-trimethyl-3H-indolium-2-yl)ethenyl]quinolinium iodide trifluoromethanesulfonate is proportional to the initial NADH concentration. Using the equation $$\Delta Abs_{535\,nm} = \varepsilon[NADH]_0 l \qquad (1),$$

an ε value for the reduced form of 1-methyl-3-[(E)-2-(1,3,3-trimethyl-3H-indolium-2-yl)ethenyl]quinolinium iodide trifluoromethanesulfonate of 69.3 mM$^{-1}$ cm$^{-1}$ was calculated from the slope of the trend line. This ε value is nine times greater than those of the reduced form of MTT (Czerlinski, G. H.; et al; Journal of Biochemical and Biophysical Methods 1988, 15, 241).

Example 13

Cyclic Voltammetry (CV) Studies of the Redoxindicators

The CVs of the compounds synthesized in example 6-7 were recorded vs. the Ag/AgCl reference electrode in a phosphate buffer pH 7 (Table 4).

TABLE 4

| Redoxindicators. CV studies | |
|---|---|
| Structure | Reduction potential (mV) |
| (XXIII) | −564 |
| (XXV) | −534 |
| (XXVI) | −524 |

TABLE 4-continued

Redoxindicators. CV studies

| Structure | Reduction potential (mV) |
|---|---|
| (XVIII) | −634 |
| (XXX) | −424 |
| (XXXI) | −454 |
| (XX) | −104, −224 |

E/mV vs Ag/AgCl, 0.9% NaCl at pH 7, phosphate buffer, Au working electrode, scan rate 100 mVs$^{-1}$

Example 14

Fluorometric Determination of NADH 13.1 Measurement 1: Change in Fluorescence Intensity Upon Reaction with NADH The following were mixed in a cuvette: 2 μL of 10 mM solution of an indicator (1-methyl-3-[(E)-2-(1,3,3-trimethyl-3H-indolium-2-yl)ethenyl]quinolinium iodide trifluoromethanesulfonate) in distilled water, 1000 μL of 10 mM PIPES buffer pH 7, 0.5-4 μL of 1 mM NADH solution in distilled water. The mixture was incubated for 30 min at room temperature. Fluorescence (550-800 nm) was recorded using excitation at 535 nm. (FIG. 10, 11).

Example 15

1-Methyl-3-[(E)-2-(1,3,3-trimethyl-3H-indolium-2-yl)ethenyl]quinolinium iodide trifluoromethanesulfonate, Evaluation of an Application for Cell Viability Testing Viable HEK-293 cells and 4% paraformaldehyde killed HEK-293 cells were incubated with 1-methyl-3-[(E)-2-(1,3,3-trimethyl-3H-indolium-2-yl)ethenyl]quinolinium iodide trifluoromethanesulfonate (20 μM) in 10 mM PBS pH 7 at 37 C. Confocal fluorescence microscope images were recorded at 611 nm using excitation at 561 nm. The image of a viable HEK-293 cell showed cellular uptake of 1-methyl-3-[(E)-2-(1,3,3-trimethyl-3H-indolium-2-yl)ethenyl]quinolinium iodide trifluoromethanesulfonate; simultaneously, the fluorescence intensity was enhanced, which is consistent with the fact that NADH was generated by the cell metabolism. The resulting cells retained viability for at least 24 h. In contrast, the paraformaldehyde treated HEK-293 cells did not show enhancement in fluorescence intensity. Therefore, fluorescence intensity upon treatment the HEK-293 cells with 1-methyl-3-[(E)-2-(1,3,3-trimethyl-3H-indolium-2-yl)ethenyl]quinolinium iodide trifluoromethanesulfonate is much higher in viable cells than in dead cells.

The work leading to this invention has received funding from the European Research Council under the European Union's Seventh Framework Program (FP7/2007-2013)/ERC grant agreement no 264772 (CHEBANA).

The invention claimed is:
1. A tricyclic chemical compound or a salt thereof, said tricyclic chemical compound comprising a tricyclic heterocyclic group covalently bound to a π-acceptor group, having the general structure of formula (I)

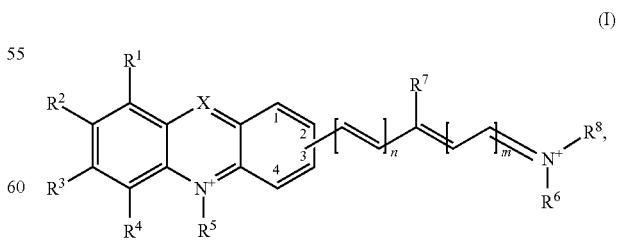

(I)

wherein
X is —CH— or —N—,
$R^1$, $R^2$, $R^3$, $R^4$ are independently selected from hydrogen; alkyl; unsubstituted or substituted aryl; halide; nitro;

sulfonate; —CN; —COOH; —OR$^9$; —SR$^9$; —SSR$^9$; —C(O)OR$^9$; —C(O)NHR$^9$; NHC(O)R$^9$; and —C(O)NH$_2$;

with R$^9$ selected from; alkyl; or unsubstituted or substituted aryl;

and/or wherein R$^a$ and R$^{a+1}$, with a=1, 2, or 3, together form a bridge to form a 5- to 6-membered cycloalkyl, aryl, heterocycloalkyl or heteroaryl ring;

R$^5$ and R$^6$ are independently selected organic side chains, n is an integer between 0 and 5, m is an integer selected from 0 and 1, R$^7$ is H or an organic side chain, R$^8$ is an organic side chain, or wherein R$^8$ and R$^7$ together form a bridge to form an, optionally substituted, 5- to 6-membered heterocycloalkyl or heteroaryl ring.

2. The tricyclic chemical compound or a salt thereof of claim 1, wherein (i) X is —N— and wherein the π-system is covalently bonded to C1, C2, C3, or C4 of the heteroaromatic system as indicated in formula (I), or (ii) X is —CH— and wherein the π-system is covalently bonded to C2 or C4 of the heteroaromatic system as indicated in formula (I).

3. The tricyclic chemical compound or a salt thereof of claim 1, wherein (i) X is —N— and wherein the π-system is covalently bonded to C1 of the heteroaromatic system as indicated in formula (I), or (ii) X is —CH— and wherein the π-system is covalently bonded to C2 of the heteroaromatic system as indicated in formula (I).

4. The tricyclic chemical compound or a salt thereof of claim 1, wherein the π-acceptor group is selected from the list consisting of (i) a side chain comprising the structure of formula (II)

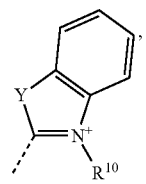

(II)

wherein Y is —N(Me)-, —S—, —Se—, —O—, or —C(Me)$_2$-, (ii) a side chain comprising the structure of formula (III)

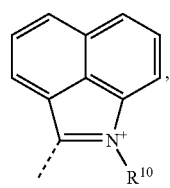

(III)

(iii) a side chain comprising the structure of formula (IV)

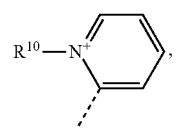

(IV)

and (iv) a side chain comprising the structure of formula (V)

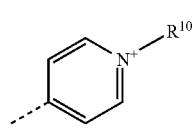

(V)

wherein in each of formulas (II) to (V), R$^{10}$ is alkyl or cycloalkyl.

5. The tricyclic chemical compound or a salt thereof of claim 1, wherein said chemical compound or a salt thereof is a compound undergoing a bathochromic shift upon reduction.

6. The tricyclic chemical compound or a salt thereof of claim 1, wherein in said chemical compound or salt thereof the π-acceptor group is not reduced by reduced coenzymes NADH, FADH, or PQQH.

7. A chemistry matrix comprising a redox cofactor and a chemical compound or a salt thereof, said chemical compound comprising a heterocyclic group (Het) covalently bound to a π-acceptor group (Acc), having the general structure of formula (VI)

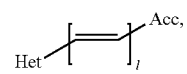

(VI)

wherein Het comprises a structure selected from formulas VII to XV:

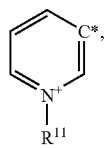

(VII)

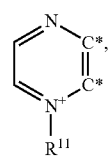

(VIII)

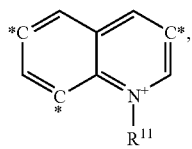

(IX)

-continued

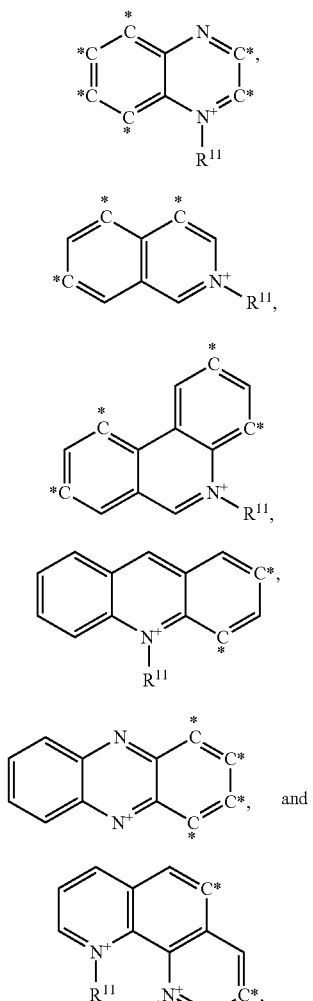

wherein R[11] is an organic side chain,
wherein the -(vinylene)$_l$Acc group is attached to one of the carbon atoms indicated as C*,
wherein l is an integer between 0 and 5,
and wherein Acc is an acceptor group of the general formula (XVI)

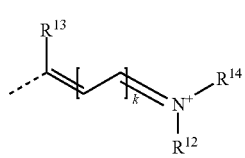

wherein
R[12] is an organic side chain,
k is an integer selected from 0 and 1,
R[13] is H or an organic side chain,
R[14] is an organic side chain,
or wherein R[13] and R[14] together form a bridge to form a 5- to 6-membered heterocycloalkyl or heteroaryl ring.

8. The chemistry matrix of claim 7, wherein said chemical compound comprises a structure of any one of (XVII) to (XXVII), (XXX) to (XXXII), and (LII):

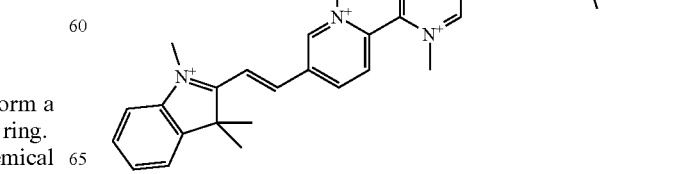

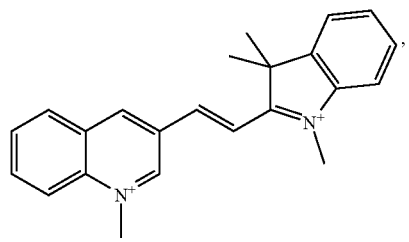 (XXV)

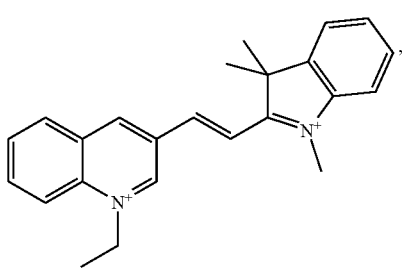 (XXVI)

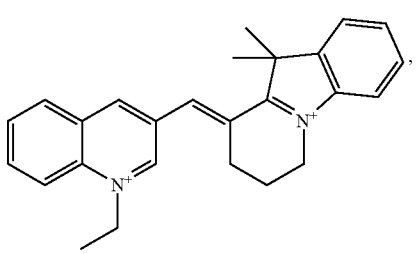 (XXVII)

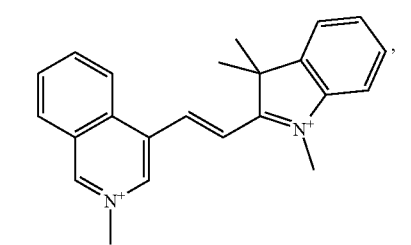 (XXX)

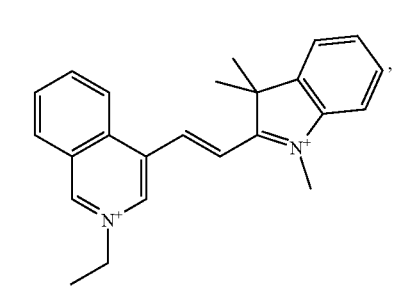 (XXXI)

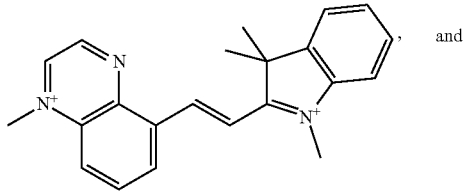 (XXXII) and

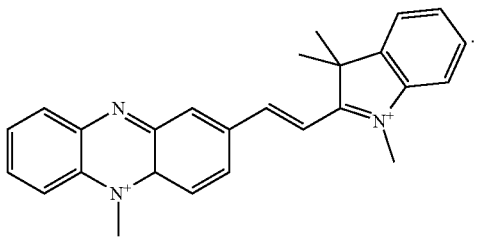 (LII)

9. The chemistry matrix of claim 7, wherein said chemical compound is 1-Methyl-6-((E)-3-oxo-3-phenyl-propenyl)-quinoline (XXII) or 1-methyl-3-[(E)-2-(1,3,3-trimethyl-3H-indolium-2-yl)ethenyl]quinoline (XXV).

10. The chemistry matrix of claim 7, further comprising an oxidoreductase enzyme.

11. The chemistry matrix of claim 7, wherein said redox cofactor is nicotine adenine dinucleotide phosphate (NADP), pyrroloquinoline quinone (PQQ), flavine adenine dinucleotide (FAD), nicotine adenine dinucleotide (NAD) or carbaNAD, or a reduced form of any of the aforesaid redox cofactors.

12. The chemistry matrix of claim 7, wherein said chemical compound is a compound undergoing a bathochromic shift upon reduction.

13. The chemistry matrix of claim 7, wherein in said chemical compound the π-acceptor group is not reduced by reduced coenzymes NADH, FADH, or PQQH.

14. A test element comprising the chemistry matrix of claim 7.

15. A system for determining the amount of an analyte in a sample, comprising
  a) a test element according to claim 14 and
  b) a device comprising a sensor for measuring the amount of redox equivalents liberated or consumed in said test element.

16. The tricyclic chemical compound or a salt thereof of claim 1, wherein said tricyclic chemical compound is 2-[(E)-2-(5-methyl-phenazin-1-yl)vinyl]-1,3,3-trimethyl-3H-indole (XX); 2-[(E)-2-(5-methyl-9-ethoxyphenazin-1-yl)vinyl]-1,3,3-trimethyl-3H-indole (XXI); or 2-[(E)-2-(5-methyl-9-ethoxyphenazin-2-yl)vinyl]-1,3,3-trimethyl-3H-indole (LII).

17. The tricyclic chemical compound or a salt thereof of claim 1 in which $R^1$, $R^2$, $R^3$, $R^4$ are independently selected from hydrogen; lower alkyl; phenyl; halide; nitro; sulfonate; —CN; —COOH; —$OR^9$; —$SR^9$; —$SSR^9$; —$C(O)OR^9$; —$C(O)NHR^9$; $NHC(O)R^9$; and —$C(O)NH_2$.

18. The tricyclic chemical compound or a salt thereof of claim 1 in which $R^9$ is selected from lower alkyl or phenyl.

19. The tricyclic chemical compound or a salt thereof of claim 1 in which each of R5, R6 and R8 is an π-acceptor group.

20. The tricyclic chemical compound or a salt thereof of claim 1 in which $R^5$ and $R^6$ are independently selected from the group consisting of methyl, ethyl and phenyl.

21. The tricyclic chemical compound or a salt thereof of claim 1 in which n is selected from the group consisting of 0, 1 and 2.

22. The tricyclic chemical compound or a salt thereof of claim 4 in which $R^{10}$ is methyl.

23. The chemistry matrix of claim 7 in which $R^{11}$ is selected from the group consisting of methyl, ethyl and phenyl.

24. The chemistry matrix of claim 7 in which l is selected from the group consisting of 0, 1 and 2.

25. The chemistry matrix of claim 8 which consists of a structure of any one of (XVII) to (XXVII), (XXX) to (XXXII) and (LII).

* * * * *